United States Patent [19]

Miller et al.

[11] Patent Number: 6,057,436
[45] Date of Patent: May 2, 2000

[54] CANINE CORONAVIRUS S GENE AND USES THEREFOR

[75] Inventors: Timothy J. Miller, Lincoln, Nebr.; Sharon Klepfer, Broomall; Albert Paul Reed, Exton, both of Pa.

[73] Assignee: Pfizer Inc., New York, N.Y.

[21] Appl. No.: 08/331,625

[22] PCT Filed: May 7, 1993

[86] PCT No.: PCT/US93/04692

§ 371 Date: Nov. 23, 1994

§ 102(e) Date: Nov. 23, 1994

[87] PCT Pub. No.: WO93/23423

PCT Pub. Date: Nov. 25, 1993

Related U.S. Application Data

[63] Continuation-in-part of application No. 07/880,194, May 8, 1992, abandoned, which is a continuation-in-part of application No. 07/698,927, May 13, 1991, abandoned, which is a continuation-in-part of application No. 07/613,066, Nov. 14, 1990, abandoned.

[51] Int. Cl.⁷ .................................................... C07H 21/04
[52] U.S. Cl. .................................... 536/23.72; 424/221.1; 424/204.1; 435/69.3; 435/320.1; 435/252.3
[58] Field of Search ............................. 424/221.1, 204.1, 424/223.1, 202.1; 435/69.3, 320.1, 252.3; 536/23.72

[56] References Cited

U.S. PATENT DOCUMENTS

| | | | |
|---|---|---|---|
| 4,567,042 | 1/1986 | Acree et al. | 424/89 |
| 4,567,043 | 1/1986 | Acree et al. | 424/89 |
| 4,824,785 | 4/1989 | Acree et al. | 435/237 |
| 4,904,468 | 2/1990 | Gill et al. | 424/89 |
| 5,013,663 | 5/1991 | Acree et al. | 435/237 |
| 5,047,238 | 9/1991 | Acree et al. | 424/89 |

FOREIGN PATENT DOCUMENTS

| | | |
|---|---|---|
| 0329264 | 8/1987 | European Pat. Off. . |
| 0264979 | 4/1988 | European Pat. Off. . |
| 0278541 | 8/1988 | European Pat. Off. . |
| 0310316 | 4/1989 | European Pat. Off. . |
| 0376744 | 7/1990 | European Pat. Off. . |
| 0396193 | 11/1990 | European Pat. Off. . |
| 0510773 | of 1992 | European Pat. Off. . |

OTHER PUBLICATIONS

Raabe et al., 1990, "Nucleotide sequence of the gene encoding the spike glycoprotein of human coronavirus HCV 229E", J. Gen. Virology 71:1065–1073.

Hohdatsu et al., 1991, "Characterization of monoclonal antibodies against feline infectious peritonitis virus type II and antigenic relationship between feline, porcine, and canine coronaviruses", Arch. Virology 117:85–95.

Bae et al., 1991, "Differentiation of transmissible gastroenteritis virus from porcine respiratory coronavirus and other antigenically related coronaviruses by using cDNA probes specific for the 5' region of the S glycoprotein gene", J. Clin. Microbiology 29:215–218.

Harlow et al., 1988, "Antibodies: a laboratory manual" Cold Spring Harbor Laboratory, pp. 313–315.

Jacobs et al., Virus Research, 8 (1987) 363–371, "The nucleotide sequence of the peplomer gene of porcine transmissible gastroenteritis virus (TGEV): comparison with the sequence of the peplomer protein of feline infectious peritonitis virus (FIPV)".

de Groot et al., J. Gen. Virology, 68 (1987) 2639–2646, "cDNA Cloning and Sequence Analysis of the Gene Encoding the Peplomer Protein of Feline Infectious Peritonitis Virus".

Luckow et al., Biotechnology, 6 (1988) 47–55, "Trends in the Development of Baculovirus Expression Vectors".

Binn et al., 1974, "Recovery and characterization of a coronavirus from military dogs with diarrhea", in: Proc. 78th Ann. Mtg. U.S. Animal Health Assoc.. Roanoke, Va., pp. 359–366.

Jacobs et al., 1987, "The nucleotide sequence of the peplomer gene of porcine transmissible gastroenteritis virus (TGEV): comparison with the sequence of the peplomer protein of feline infectious peritonitis virus (FIPV)", Virus Res. 8:363–371.

Takahashi et al., 1990, "Induction of $CD8^+$ cytotoxic T cells by immunization with purified HIV–1 envelope protein in ISCOMs", Nature 344:873–875.

Vennema et al., 1990, "Early death after feline infectious peritonitis virus challenge due to recombinant vaccinia virus immunization", J. Virology 64:1407–1409.

Spaan, 1990, "Progress towards a coronavirus recombinant DNA vaccine", in: *Coronaviruses and their diseases*, Cavanagh and Brown (eds), Plenum Press, N.Y. pp. 201–203.

Young et al., 1983, "Efficient isolation of genes by using antibody probes", Proc. Natl. Acad. Sci. USA 80:1194–1198.

Lerner et al., 1983, "The development of synthetic vaccines", in: *The biology of immunologic disease*, Dixon and Fisher (eds), Sinauer Associates Publishing Co., Ma., pp. 331–338.

*Primary Examiner*—Laurie Scheiner
*Attorney, Agent, or Firm*—Peter C. Richardson; Paul H. Ginsburg; E. Victor Donahue

[57] ABSTRACT

The present invention provides the amino acid and nucleotide sequences of a CCV spike gene, and compositions containing one or more fragments of the spike gene for prophylaxis, diagnostic, and treatment of CCV infections.

9 Claims, No Drawings

CANINE CORONAVIRUS S GENE AND USES THEREFOR

CROSS-REFERENCE TO RELATED APPLICATION

This application is a 371 of PCT/U.S. 93/04692, which is a continuation-in-part of U.S. patent application Ser. No. 07/880,194, filed May 8, 1992 abandoned, which is a continuation-in-part of U.S. patent application Ser. No. 07/698,927, filed May 13, 1991 abandoned, which is a continuation-in-part of U.S. patent application Ser. No. 07/613,066, filed Nov. 14, 1990, abandoned.

FIELD OF THE INVENTION

The present invention relates generally to canine coronavirus infections, and specifically to proteins useful in prophylaxis, therapy, and diagnosis of these infections in canines.

BACKGROUND OF THE INVENTION

The coronaviruses are a large family of mammalian and avian pathogens which were first described in 1968. They are the causative agents of several diseases including encephalitis, hepatitis, peritonitis and gastroenteritis. Enteric coronaviruses have been detected in the feces of man, pigs, calves, cats, mice, chickens and dogs.

Canine coronavirus (CCV) enteritis was first isolated from dogs suffering an acute gastroenteritis, as reported by Binn et al., *Proc. 78th Ann. Mtg. U.S. Animal Health Assoc.*, Roanoke Va., pp. 359–366 (1974). The disease became prevalent during the 1970s. CCV gastroenteritis appears to be primarily transmitted through fecal contamination from infected dogs via the oral route, leading ultimately to replication of the virus in the epithelial cells of the small intestine. Virus can be recovered from the feces of an infected dog between 3 and 14 days after infection.

CCV gastroenteritis is characterized by a mild depression, anorexia and loose stool from which the dog usually recovers. The onset of the disease is often sudden, accompanied by such symptoms as diarrhea, vomiting, excreted blood in stools, and dehydration. Deaths have occurred within as little as 24 to 36 hours after onset of clinical signs. Most dogs appear afebrile but elevated body temperature is seen in some cases. Often CCV will occur with a canine parvovirus infection and this coinfection can be fatal.

Serologically the disease is closely related to transmissible gastroenteritis virus of swine (TGEV). Although canine coronavirus does not infect pigs, transmissible gastroenteritis virus produces a subclinical infection in dogs. However, unlike the feline infectious peritonitis coronavirus (FIPV), previous exposure to CCV does not predispose dogs to enhanced disease; and antigen-antibody complexes, if formed, are not associated with disease pathology.

There remains a need in the art for compositions useful in diagnosing, treating and preventing infections with canine coronaviruses.

SUMMARY OF THE INVENTION

In one aspect the present invention provides the complete nucleotide sequence of the CCV S gene, strain 1-71, SEQ ID NO:1. The S gene or fragments thereof may be useful in diagnostic compositions for CCV infection.

In another aspect the present invention provides a CCV S (or spike) protein characterized by the amino acid sequence of a CCV S protein, SEQ ID NO:2, and peptide fragments thereof. These proteins may be optionally fused or linked to other fusion proteins or molecules.

Thus, in another aspect, the present invention provides a vaccine composition containing an effective immunogenic amount of at least one CCV S protein or an immunogenic fragment thereof.

In still another aspect, the invention provides a method of vaccinating an animal against infection with a coronavirus by administering an effective amount of a vaccine composition of this invention.

In yet a further aspect, the present invention provides a pharmaceutical composition for the treatment of CCV infection comprising a therapeutically effective amount of a CCV S peptide or protein of the invention and a pharmaceutically effective carrier.

Still another aspect of this invention is an antibody directed to CCV, which antibody is capable of distinguishing between CCV and other canine viruses. These antibodies may also be employed as diagnostic or therapeutic reagents.

In yet another aspect, a diagnostic reagent of the present invention comprises a CCV S protein or fragment thereof. In another aspect, the present invention provides a diagnostic reagent which comprises a nucleotide sequence which encodes a CCV S protein or fragment of the invention, and/or a nucleotide sequence which flanks the coding region, or fragments thereof. These protein and nucleotide sequences are optionally associated with detectable labels. Such diagnostic reagents may be used to assay for the presence of CCV in dogs using standard assay formats and can form components of a diagnostic kit.

In a further aspect, the invention provides a method of using a diagnostic reagent of this invention to identify dogs which are uninfected or which have been previously exposed to CCV. The diagnostic method can differentiate exposure to CCV from exposure to other related coronaviruses, allow the identification of dogs which have been vaccinated against these diseases, and allow one to distinguish between different strains of CCV, or to identify dogs at advanced stages of CCV infection.

In yet a further aspect, the invention provides a method for the production of a recombinant CCV protein comprising culturing a selected host cell, e.g., a mammalian cell or viral vector, transformed with a DNA sequence encoding a selected CCV S protein or fragment thereof in operative association with regulatory sequences capable of regulating the expression of said protein.

Another aspect of the invention is a recombinant DNA molecule comprising a DNA sequence coding for a selected portion of a canine coronavirus S protein, the DNA sequences in operative association with regulatory sequences capable of directing the expression thereof in host cells.

Other aspects and advantages of the present invention are described further in the following detailed description of the preferred embodiments thereof.

DETAILED DESCRIPTION OF THE INVENTION

The present invention provides novel isolated canine coronavirus (CCV) S proteins and fragments thereof, as well as isolated nucleotide sequences encoding the proteins or fragments. These proteins and fragments are useful for diagnostic, vaccinal and therapeutic compositions as well as methods for using these compositions in the diagnosis, prophylaxis and treatment of CCV-related and other coronavirus-related conditions.

I. Definitions

As defined herein, an amino acid fragment is any amino acid sequence from at least about 8 amino acids in length up to about the full-length CCV S gene protein. A nucleotide fragment defines a nucleotide sequence which encodes from at least about 8 amino acids in length up to about the full-length CCV S gene protein.

The term "region" refers to all or a portion of a gene or protein, which may contain one or more fragments as defined above.

The term "immunogenic" refers to any S gene protein or fragment thereof, any molecule, protein, peptide, carbohydrate, virus, region or portion thereof which is capable of eliciting a protective immune response in a host, e.g., an animal, into which it is introduced.

The term "antigenic" refers only to the ability of a molecule, protein, peptide, carbohydrate, virus, region or portion thereof to elicit antibody formation in a host (not necessarily protective).

As used herein, the term "epitope" refers to a region of a protein which is involved in its immunogenicity, and can include regions which induce B cell and/or T cell responses.

As used herein, the term "B cell site or T cell site" defines a region of the protein which is a site for B cell or T cell binding. Preferably this term refers to sites which are involved in the immunogenicity of the protein.

II. Sources of CCV Sequences

The examples below specifically refer to newly identified spike gene sequences from canine coronavirus (CCV) strain 1-71. This strain is deposited with the American Type Culture Collection (ATCC), 12301 Parklawn Drive, Rockville, Md. under Accession No. VR-809. Particularly disclosed are nucleotide and amino acid sequences, SEQ ID NO:1 and 2, respectively, of the CCV S gene.

The present invention is not limited to the particular CCV strain employed in the examples. Other CCV strains have been described, e.g., strain CCV-TN449 [ATCC 2068]. Utilizing the teachings of this invention, analogous fragments of other canine coronavirus strains can be identified and used in the compositions of this invention.

III. CCV Nucleotide and Amino Acid Sequences of the Invention.

The inventors have identified and selected nucleotide and protein sequences of CCV strain 1-71 which have been determined to be of interest for use as vaccinal, therapeutic and/or diagnostic compositions. For example, selected peptide and nucleotide sequences present primarily in the variable N terminal region of the CCV S protein and gene are characterized by representing areas of homology between FIPV, TGEV, feline enteric coronavirus (FECV) and other coronavirus strains.

Peptide fragments obtained from this heterogeneous N terminal of the S protein are useful fragments for diagnostic compositions and kits for distinguishing between infection with CCV strain 1-71 from other CCV infections, and for distinguishing between infection with CCV and other coronavirus identified above in a vaccinated or infected dog, as well as for use in vaccine and therapeutic agents.

Additionally, the amino terminal sequences of CCV S protein include peptide sequences which are B cell sites and thus useful in vaccinal or therapeutic compositions, or for generating antibodies to CCV, in assays for the detection of CCV antibodies in dogs.

In addition, certain peptide fragments of the CCV S protein are believed to represent T cell sites, and thus are useful in vaccinal or therapeutic compositions.

Other suitable CCV amino acid regions for pharmaceutical or diagnostic use are located within other regions of the CCV S protein SEQ ID NO: 2. These amino acid and nucleotide fragments of the CCV S protein and its nucleotide sequence discussed above are specifically reported below in Tables I and II. Table II also reports the respective homologies of certain of these desired fragments to wild-type FIPV, i.e., FIPV WSU 1146. The CCV S nucleotide fragments in Tables I and II can be useful for diagnostic probes, PCR primers, or for use in recombinant production of relevant S protein fragments for use in therapeutic or vaccinal compositions. Other suitable fragments may also be identified for such use.

TABLE I

| CCV Amino Acids | | |
|---|---|---|
| B cell sites | T cell sites | SEQ ID NOS: |
| 50–250 | | 3 |
| 375–425 | | 4 |
| 450–470 | | 5 |
| 550–600 | | 6 |
| 650–700 | | 7 |
| 770–850 | | 8 |
| 900–1025 | | 9 |
| 1150–1225 | | 10 |
| 1250–1452 | | 11 |
| | 40–47 | 12 |
| | 63–81 | 13 |
| | 187–191 | 14 |
| | 241–274 | 15 |
| | 335–341 | 16 |
| | 395–428 | 17 |
| | 468–494 | 18 |
| | 846–860 | 19 |
| | 916–952 | 20 |
| | 977–992 | 21 |
| | 1068–1145 | 22 |
| | 1366–1391 | 23 |

TABLE II

| Amino Acid Sequences | | | |
|---|---|---|---|
| CCV 1-71 | | % Homology CCV 1-71 | SEQ ID NOS. |
| Amino Acid | Nucleotides | to WT FIPV WSU 1146 | AA Nucl. |
| 1113–1236 | 3337–3708 | 100 | 25 and 24 |
| 540–599 | 1618–1797 | 93.3 | 27 and 26 |
| 342–388 | 1024–1164 | 93.6 | 29 and 28 |
| 137–153 | 409–459 | 64.7 | 31 and 30 |
| 375–388 | 1123–1164 | 85.7 | 33 and 32 |
| 1424–1440 | 4270–4320 | 94.1 | 35 and 34 |
| 1407–1420 | 4219–4260 | 85.7 | 37 and 36 |
| 1342–1406 | 4024–4218 | 96.9 | 39 and 38 |
| 398–652 | 1192–1956 | 93.3 | 41 and 40 |
| 128–555 | 382–1665 | 89.5 | 43 and 42 |
| 447–628 | 1339–1884 | 91.8 | 45 and 44 |

IV. Modified Sequences of the Invention.

In addition to the amino acid sequences and corresponding nucleotide sequences of the specifically-recited embodiments of CCV S proteins of this invention, the invention also encompasses other DNA and amino acid sequences of CCV S proteins. Such other nucleic acid sequences include those sequences capable of hybridizing to SEQ ID NO: 1 under conditions of at least 85% stringency, i.e. having at least 85% homology to the sequence of SEQ ID NO: 1, more preferably at least 90% homology, and most preferably at least 95% homology. Such homologous sequences are characterized by encoding a CCV S gene protein related to strain 1-71.

Further, allelic variations (naturally-occurring base changes in the species population which may or may not result in an amino acid change) of DNA sequences encoding the various S amino acid or DNA sequences from the illustrated CCV are also included in the present invention, as well as analogs or derivatives thereof. Similarly, DNA sequences which code for protein sequences of the invention but which differ in codon sequence due to the degeneracies of the genetic code or variations in the DNA sequence encoding these proteins which are caused by point mutations or by induced modifications to enhance the activity, half-life or production of the peptide encoded thereby are also encompassed in the invention.

Variations in the amino acid sequences of this invention may typically include analogs that differ by only 1 to about 4 codon changes. Other examples of analogs include polypeptides with minor amino acid variations from the natural amino acid sequence of S gene proteins and/or the fusion partner; in particular, conservative amino acid replacements. Conservative replacements are those that take place within a family of amino acids that are related in their side chains. Genetically encoded amino acids are generally divided into four families: (1) acidic=aspartate, glutamate; (2) basic=lysine, arginine, histidine; (3) non-polar=alanine, valine, leucine, isoleucine, proline, phenylalanine, methionine, tryptophan;

and (4) uncharged polar=glycine, asparagine, glutamine, cysteine, serine, threonine, tyrosine. Phenylalanine, tryptophan, and tyrosine are sometimes classified jointly as aromatic amino acids. For example, it is reasonable to expect that an isolated replacement of a leucine with an isoleucine or valine, an aspartate with a glutamate, a threonine with a serine, or a similar conservative replacement of an amino acid with a structurally related amino acid will not have a significant effect on its activity, especially if the replacement does not involve an amino acid at an epitope of the polypeptides of this invention.

V. Fusion Proteins.

If desired, the CCV S proteins and peptide fragments, e.g. those identified in Tables I and II, can be produced in the form of fusion proteins as defined below. Such a fusion protein may contain either a full-length CCV S protein or an immunogenic fragment thereof. Suitable fragments include those contained within SEQ ID NO: 2 and the amino acids fragments of Tables I and II. Other suitable fragments can be determined by one of skill in the art by analogy to the sequences provided herein.

Proteins or peptides may be selected to form fusion proteins with the selected S protein or peptide sequence based on a number of considerations. The fusion partner may be a preferred signal sequence, a sequence which is characterized by enhanced secretion in a selected host cell system, or a sequence which enhances the stability or presentation of the S-derived peptide. Such exemplary fusion partners include, without limitation, ubiquitin and a mating factor for yeast expression systems, and beta-galactosidase and influenza NS-1 protein for bacterial systems. One of skill in the art can readily select an appropriate fusion partner for a selected expression system. The present invention is not limited to the use of any particular fusion partner.

The CCV S protein or fragments thereof can optionally be fused to each other or to the fusion partner through a conventional linker sequence, i.e., containing about 2 to 50 amino acids, and more preferably, about 2 to about 20 amino acids in length. This optional linker may provide space between the two linked sequences. Alternatively, this linker sequence may encode, if desired, a polypeptide which is selectively cleavable or digestible by conventional chemical or enzymatic methods. For example, the selected cleavage site may be an enzymatic cleavage site, including sites for cleavage by a proteolytic enzyme, such as enterokinase, factor Xa, trypsin, collagenase and thrombin. Alternatively, the cleavage site in the linker may be a site capable of being cleaved upon exposure to a selected chemical, e.g., cyanogen bromide or hydroxylamine. The cleavage site, if inserted into a linker useful in the fused sequences of this invention, does not limit this invention. Any desired cleavage site, of which many are known in the art, may be used for this purpose.

VI. Production of Sequences of Invention

The CCV S gene protein of the invention and amino acid regions, fragments thereof and their corresponding nucleotide sequences, as well as other proteins described herein, e.g. fusion partners, may be produced by conventional methods. These proteins or fragments and the nucleotide sequences may be prepared by chemical synthesis techniques [Merrifield, *J.A.C.S.*, 85:2149–2154 (1963)]. Preferably, however, they are prepared by known recombinant DNA techniques by cloning and expressing within a host microorganism or cell a DNA fragment carrying a coding sequence for the selected protein. See, e.g., Sambrook et al, "Molecular Cloning. A Laboratory Manual", 2nd edit., Cold Spring Harbor Laboratory, New York (1989). Such techniques are discussed below in the Examples.

According to cloning techniques, a selected gene fragment of this invention can be cloned into a selected expression vector. Vectors for use in the method of producing S protein proteins comprise a novel S gene DNA sequence (or a fragment thereof) of the invention and selected regulatory sequences in operative association with the DNA coding sequence, and capable of directing the replication and expression of the peptide in a selected host cell.

Vectors, e.g., polynucleotide molecules, of the invention may be designed for expression of CCV S proteins and/or fusion proteins in bacterial, mammalian, fungal or insect cells or in selected viruses. Suitable vectors are known to one skilled in the art by resort to known publications or suppliers.

The resulting DNA molecules or vectors containing nucleotide sequences encoding the canine coronavirus S peptides or fragments thereof and/or encoding the fusion proteins are then introduced into host cells and expression of the heterologous protein induced.

Additional expression systems may include the known viral expression systems, e.g., vaccinia, fowlpox, swine pox. It is understood additionally, that the design of the expression vector will depend on the choice of host cell. A variety of suitable expression systems in any of the below-identified host cells are known to those skilled in the art and may be readily selected without undue effort.

Suitable cells or cell lines for use in expressing the S protein or peptides of this invention can be eukaryotic or prokaryotic. A preferred expression system includes mammalian cells, such as Chinese Hamster ovary cells (CHO) or COS-1 cells. The selection of other suitable mammalian host cells and methods for transformation, culture, amplification, screening and product production and purification are known in the art. See, e.g., Gething and Sambrook, *Nature*, 293:620–625 (1981), or alternatively, Kaufman et al, *Mol. Cell. Biol.*, 5(7):1750–1759 (1985) or Howley et al, U.S. Pat. No. 4,419,446. Also desirable are insect cell systems, such as the baculovirus or Drosophila systems. The selection of other suitable host cells and methods for transformation, culture, amplification, screening and product production and purification can be performed by one of skill in the art by reference to known techniques. See, e.g., Gething and Sambrook, *Nature*, 293:620–625 (1981).

After the transformed host cells are conventionally cultured for suitable times and under suitable culture conditions known to those skilled in the art, the cells may be lysed. It may also be possible, depending on the construct employed, that the recombinant proteins are secreted extracellularly and obtained from the culture medium. Cell lysates or culture medium are then screened for the presence of CCV S protein or peptide which are recognized by antibodies, preferably monoclonal antibodies (MAbs), to a peptide antigenic site from CCV.

Similarly, the fusion proteins may be produced by resort to chemical synthesis techniques, or preferably, recombinant methods, as described above. The selected primer sets used in the PCR reaction described in the Examples below may be designed to produce PCR amplified fragments containing restriction endonuclease cleavage site sequences for introduction of a canine coronavirus S gene fragment in a specific orientation into a selected expression vector to produce fusion proteins of the invention. The vector may contain a desired protein or fragment thereof to which the S gene fragment is fused in frame to produce a fusion protein.

The crude cell lysates containing the CCV S protein or peptides or fusion proteins can be used directly as vaccinal components, therapeutic compositions or diagnostic reagents. Alternatively, the CCV S peptides can be purified from the crude lysate or medium by conventional means.

VII. Vaccine Compositions

The CCV S proteins and immunogenic fragments of this invention may be incorporated in a vaccine composition. Such a vaccine composition may contain an immunogenic amount of one or more selected CCV S peptides or proteins, e.g., encoded by the complete S gene sequence of CCV or partial sequences thereof, and prepared according to the method of the present invention, together with a carrier suitable for administration as a vaccine composition for prophylactic treatment of CCV infections. The protein may be in the form of a fusion protein as above-described. Alternatively, the CCV S gene or fragment may be incorporated into a live vector, e.g., adenovirus, vaccinia virus and the like. The expression of vaccinal proteins in such live vectors are well-known to those in the art [See, e.g., U.S. Pat. No. 4,920,209]. It is preferable that the protein employed in the vaccine composition induces protective immune responses against more than one strain of CCV.

A vaccine composition according to the invention may optionally contain other immunogenic components. Particularly desirable are vaccine compositions containing other canine antigens, e.g., canine distemper, *Borrelia burgdorferi*, canine Bordetella, rabies, canine parvovirus, Leptosporidia sp., canine rotavirus, canine parainfluenza virus and canine adenovirus.

In another embodiment, the CCV S proteins may be used in a combination vaccine directed to related coronaviruses. Other suitable coronaviruses which can be used in such a combination vaccine include a feline coronavirus, such as FIPV or FECV. For example, a CCV S peptide or protein of the present invention may be employed as an additional antigen in the temperature sensitive FIPV vaccine described in detail in co-owned, co-pending U.S. patent application Ser. No. 07/428,796 filed Oct. 30, 1989, incorporated by reference herein. Alternatively, the CCV S protein or peptide or a fragment thereof could be used in a vaccine composition containing other coronavirus S proteins or fragments thereof, particularly those described in co-pending, co-owned U.S. patent application Ser. No. 07/698,927 (and its corresponding published PCT Application No. W092/08487).

The preparation of a pharmaceutically acceptable vaccine composition, having appropriate pH isotonicity, stability and other conventional characteristics is within the skill of the art. Thus such vaccines may optimally contain other conventional components, such as adjuvants and/or carriers, e.g. aqueous suspensions of aluminum and magnesium hydroxides, liposomes and the like.

The vaccine composition may be employed to vaccinate animals against the clinical symptoms associated with CCV. The vaccines according to the present invention can be administered by an appropriate route, e.g., by the oral, intranasal, subcutaneous, intraperitoneal or intramuscular routes. The presently preferred methods of administration are the subcutaneous and intranasal routes.

The amount of the CCV S peptide or protein of the invention present in each vaccine dose is selected with regard to consideration of the animal's age, weight, sex, general physical condition and the like. The amount required to induce an immunoprotective response in the animal without significant adverse side effects may vary depending upon the recombinant protein employed as immunogen and the optional presence of an adjuvant. Generally, it is expected that each dose will comprise between about 0.05–5000 micrograms of protein per mL, and preferably 0.05–100 micrograms per mL of a sterile solution of an immunogenic amount of a protein or peptide of this invention. Initial doses may be optionally followed by repeated boosts, where desirable.

Another vaccine agent of the present invention is an anti-sense RNA sequence generated to the S gene of CCV strain 1-71 [SEQ ID NO:1] [S. T. Crooke et al, *Biotech.*, 10:882–886 (August 1992)]. This sequence may easily be generated by one of skill in the art either synthetically or recombinantly. Under appropriate delivery, such an anti-sense RNA sequence when administered to an infected animal should be capable of binding to the RNA of the virus, thereby preventing viral replication in the cell.

VIII. Pharmaceutical Compositions

The invention also provides a pharmaceutical composition comprising one or more CCV S peptides or proteins prepared according to the present invention and a pharmaceutically effective carrier. Suitable pharmaceutically effective carriers for internal administration are known to those skilled in the art. One selected carrier is sterile saline. The pharmaceutical composition can be adapted for administration by any appropriate route, but is designed preferentially for administration by injection or intranasal administration.

IX. Antibodies of the Invention

The present invention also encompasses the development of an antibody to one or more epitopes in the above identified amino acid sequences derived from the CCV S protein, which epitope is distinct from those of other CCV strains or other coronaviruses, e.g. FIPV, TGEV or FECV. The antibody can be developed employing as an antigenic substance, a peptide of Table I or II. Alternatively, other regions of the CCV strain 1-71 S protein SEQ ID NO: 2 may be employed in the development of an antibody according to conventional techniques.

In one embodiment, the antibody is capable of identifying or binding to a CCV antigenic site encoded by SEQ ID NO: 1 or a fragment thereof. Such an antibody may be used in a diagnostic screening test, e.g., as a hybridization probe, or as a therapeutic agent.

Antibodies which bind CCV peptides from the regions identified above or to other regions capable of distinguishing between CCV, TGEV, FIPV, FECV, and other coronaviruses for use in the assays of this invention may be polyclonal. However, it is desirable for purposes of increased target specificity to utilize MAbs, both in the assays of this invention and as potential therapeutic and prophylactic agents. Additionally, synthetically designed MAbs may be made by known genetic engineering techniques [W. D. Huse et al, *Science*, 246:1275–1281 (1989)] and employed in the methods described herein. For purposes of simplicity the term MAb(s) will be used throughout this specification; however, it should be understood that certain polyclonal antibodies, particularly high titer polyclonal antibodies and recombinant antibodies, may also be employed.

A MAb may be generated by the well-known Kohler and Milstein techniques and modifications thereof and directed to one or more of the amino acid residue regions identified above, or to other CCV S peptides or epitopes containing differences between CCV strain 1-71 and other coronaviruses. For example, a fragment of SEQ ID NO: 2 which represents an antigenic site, which differs from that of FIPV, may be presented as an antigen in conventional techniques for developing MAbs. One of skill in the art may generate any number of MAbs by using fragments of the amino acid residue regions identified herein as an immunogen and employing these teachings.

For diagnostic purposes, the antibodies (as well as the diagnostic probes) may be associated with individual labels. Where more than one antibody is employed in a diagnostic method, the labels are desirably interactive to produce a detectable signal. Most desirably, the label is detectable visually, e.g. colorimetrically. Detectable labels for attachment to antibodies useful in the diagnostic assays of this invention may also be easily selected by one skilled in the art of diagnostic assays, amont which include, without limitation, horseradish peroxidase (HRP) or alkaline phosphatase (AP), hexokinase in conjunction with glucose-6-phosphate dehydrogenase, and NAD oxidoreductase with luciferase and substrates NADH and FMN or peroxidase with luminol and substrate peroxide. These and other appropriate label systems and methods for coupling them to antibodies or peptides are known to those of skill in the art.

Antibodies may also be used therapeutically as targeting agents to deliver virus-toxic or infected cell-toxic agents to infected cells. Rather than being associated with labels for diagnostic uses, a therapeutic agent employs the antibody linked to an agent or ligand capable of disabling the replicating mechanism of the virus or of destroying the virally-infected cell. The identity of the toxic ligand does not limit the present invention. It is expected that preferred antibodies to peptides encoded by the S genes identified herein may be screened for the ability to internalize into the infected cell and deliver the ligand into the cell.

X. Diagnostic Reagents and Assays

The nucleotide sequences, amino acid fragments and antibodies described above may be employed as diagnostic reagents for use in a variety of diagnostic methods according to this invention.

A. PCR Diagnostic Assays.

For example, these sequences can be utilized in a diagnostic method employing the polymerase chain reaction (PCR) technique to identify the presence of a CCV or CCV-like virus and in therapy of infected animals.

In addition to those sequences identified above, the oligonucleotide sequences that were designed to prime cDNA synthesis at specific sites within the CCV S gene, as described in detail below in Example 3 [SEQ ID NO:46–50], may also be employed as diagnostic reagents according to this invention. These sequences, as well as the below-described optimized conditions for the PCR amplification of CCV fragments therefrom, may also be employed in a diagnostic method.

The PCR technique is known to those of skill in the art of genetic engineering and is described in detail in Example 4 [see, e.g., R. K. Saiki et al, *Science*, 230:1350–1354 (1985)], which is incorporated herein by reference. Briefly described, PCR employs two oligonucleotide primers which are complementary to the opposite strands of a double stranded nucleic acid of interest whose strands are oriented such that when they are extended by DNA polymerase, synthesis occurs across the region which separates the oligonucleotides. By repeated cycles of heat denaturation, annealing of the primers to their complementary sequences and extension of the annealed primers with a temperature stable DNA polymerase, millions of copies of the target gene sequence are generated. The template for the reaction is total RNA, which is isolated from CCV infected cells. DNA fragments generated by PCR were amplified from CDNA which had been synthesized from this RNA. Other strains of CCV or CCV-related sequences may also provide PCR templates in a similar manner.

In one diagnostic method, for example, heterogenous CCV gene sequences of this invention are useful as reagents in diagnostic assays to detect and distinguish the presence of specific viruses from each other, e.g., to distinguish one canine coronavirus strain from another or one species of coronavirus from another by means of conventional assay formats. For example, using protocols similar to those used for forensic purposes, tissue or blood samples from a dog suspected to be infected with CCV would be subjected to PCR amplification with a selected CCV-specific set of primers, such as those DNA sequences disclosed herein. Amplification of DNA from a sample tissue or biological fluid of the animal suspected of infection using nucleotide sequences as primers specific for regions of the CCV viral gene sequences could correlate to the presence of CCV. Absence of CCV in the sample would result in no amplification. Similarly, the selection of specific sets of S gene primers would allow the identification of a particular strain of CCV as well. Thus, appropriate treatments may be selected for the infected animal.

Example 3 provides oligonucleotide primers which permitted the synthesis of regions of the CCV S gene. The nucleotide sequence of the S gene of CCV provides desirable sequences for hybridization probes and PCR primers, for example, the sequences between nucleotide base pairs 900 to about 1600 [SEQ ID NO: 55] and about 2500 to about 3900 [SEQ ID NO: 56] of SEQ ID NO: 1. Smaller or larger DNA fragments in these regions may also be employed as PCR primers or hybridization probes.

It is desirable to have PCR primer sequences between 15 to 30 bases in length, with an intervening sequence of at least 100 bases to as large as 5000 bases there between, according to conventional PCR technology. However, it is possible that larger or smaller sequence lengths may be useful based upon modifications to the PCR technology. In general, in order to achieve satisfactory discrimination, a hybridization or oligonucleotide probe made up of one or more of these sequences would consist of between 15 and 50 bases in length based on current technology.

B. Conventional Assay Formats

The CCV S proteins or peptide fragments may also be employed in standard diagnostic assays which rely on S protein immunogens as targets for sera recognition. The diagnostic assays may be any conventionally employed assay, e.g., a sandwich ELISA assay, a Western blot, a Southern blot and the like. Because a wide variety of diagnostic methods exist and are conventionally known which can be adapted to the use of the nucleotide and amino acid sequences described herein, it should be understood that the nature of the diagnostic assay does not limit the use of the sequences of this invention.

For example, the amino acid sequences encoded by CCV S gene sequences, such as those appearing in Tables I and II above, which may be amplified by PCR, provide peptides useful in such diagnostic assays as ELISA or Western assay, or as antigens for the screening of sera or development of antibodies.

For example, the sequences between about amino acid 1 to about 250 [SEQ ID NO:57], about 450 to about 650 [SEQ ID NO:58], and about 900 to about 1150 [SEQ ID NO:59] of the CCV strain 1-71 S gene protein SEQ ID NO:2, are anticipated to be useful as such antigens. Such peptides can optionally also be used in the design of synthetic peptide coupled to a carrier for diagnostic uses, e.g., antibody detection in sera. Suitable carriers include ovalbumin, keyhole limpet hemocyanin, bovine serum albumin, sepharose beads and polydextran beads.

Such peptide antigens and antibodies to these peptides would react positively with tissue or serum samples of dogs infected with CCV, but negatively with non-CCV infected dogs. These antibodies are discussed in more detail below.

For example, the invention provides a method of using the full length CCV S protein or fragments thereof as diagnostic agents for identifying the presence or absence of antibodies in previously exposed, naive or vaccinated dogs, respectively, as well as for differentiating exposure to CCV from other related coronaviruses. Other S peptides or fusion proteins which show differential reactivity to CCV and other coronavirus sera may also be useful as CCV-specific reagents in ELISA-based screening assays to detect CCV exposure in dogs. Similarly, an S protein or peptide which contains epitopes recognized only by sera from CCV infected dogs or by sera from CCV positive dogs could be employed to distinguish or differentiate among coronavirus infections.

As one assay format, the reactivity of affinity purified CCV S proteins or peptides fragments to canine biological fluids or cells can be assayed by Western blot. The assay is preferably employed on sera, but may also be adapted to be performed on other appropriate fluids or cells, for example, macrophages or white blood cells. In the Western blot technique, the purified protein, separated by a preparative SDS polyacrylamide gel, is transferred to nitrocellulose and cut into multiple strips. The strips are then probed with dog sera from uninfected or infected dogs. Binding of the dog sera to the protein is detected by incubation with alkaline phosphatase tagged goat anti-dog IgG followed by the enzyme substrate BCIP/NBT. Color development is stopped by washing the strip in water.

CCV S protein or fragments thereof may also be used in an ELISA based assay for detecting CCV disease. A typical ELISA protocol would involve the adherence of antigen (e.g., a S protein) to the well of a 96-well tray. The serum to be tested is then added. If the serum contains antibody to the antigen, it will bind. Specificity of the reaction is determined by the antigen absorbed to the plate. With the S protein, only sera from those dogs infected with CCV would bind to the plate; sera from naive or uninfected dogs would not bind. Similarly, a CCV S protein or peptide which contained epitopes recognized only by sera from CCV-infected dogs or by sera from CCV-positive dogs could be employed to distinguish coronavirus infections. After the primary antibody is bound, an enzyme-labeled antibody directed against the globulin of the animal whose serum is tested is added. Substrate is then added. The enzyme linked to antibody bound to the well will convert the substrate to a visible form. The amount of color measured is proportional to the amount of antibody in the test material. In this manner, dogs infected with CCV can be identified and treated, or dogs naive to the virus can be protected by vaccination.

When used as diagnostic reagents, the primers, probes, peptide antigens, nucleotide sequence encoding or flanking a CCV S protein or fragment of the invention, and antibodies of this invention may be optionally associated with detectable labels or label systems known to those skilled in the art. Such labelled diagnostic reagents may be used to assay for the presence of CCV in dogs in hybridization assays or in the PCR technique as described above.

C. Diagnostic Kits

The assay methods, PCR primers, CCV S nucleotide sequences [SEQ ID NO:1], S proteins and peptides, and antibodies described herein may be efficiently utilized in the assembly of a diagnostic kit, which may be used by veterinarians or laboratories. The kit is useful in distinguishing between CCV infected animals and vaccinated animals, as well as non-exposed dogs, and between CCV-infected animals and animals infected with serologically related viruses, such as other CCV or FIPV, TGEV, and FECV. Such a diagnostic kit contains the components necessary to practice the assays described above.

Thus, the kit may contain a sufficient amount of at least one CCV S protein, fusion protein or peptide fragment, at least one CCV S gene nucleotide sequence or PCR primer pair of this invention, a MAb directed to a first epitope on the CCV S protein (which MAb may be labeled), optional additional components of a detectable labelling system, vials for containing the serum samples, protein samples and the like, and a second MAb conjugated to the second enzyme, which in proximity to the first enzyme, produces a visible product. Other conventional components of such diagnostic kits may also be included.

Alternatively, a kit may contain a selected CCV S protein or peptide, a MAb directed against a selected CCV S peptide fragment bound to a solid surface and associated with a first enzyme, a different MAb associated with a second enzyme, and a sufficient amount of the substrate for the first enzyme, which, when added to the serum and MAbs, provides the reactant for the second enzyme, resulting in the color change.

Other known assay formats will indicate the inclusion of additional components for a diagnostic kit according to this invention.

The following examples illustrate the embodiments of this invention and do not limit the scope of the present invention.

EXAMPLE 1

ISOLATION OF CCV

Canine coronavirus strain 1-71 was isolated in 1971 from military dogs suffering from a viral gastroenteritis by Binn et al., *Proceeding 78th Annual Meeting U.S. Animal Health Association*, October 1974, p. 359–366. The initial isolate from the feces of the infected dog was grown in tissue culture on the PrDKTCA72 dog cell line [ATCC No. CRL 1542]. The coronavirus strain used in this study was received from the ATCC (ATCC #VR-809, CCV Strain 1-71, Frozen lot#4, Passage 7/PDK, 17 May 1988) and passaged five times on PrDKTCA72.

EXAMPLE 2

RNA Purification

After the fifth passage the infected cells were processed for RNA isolation by infecting a 1700 cc$^2$ roller bottle with a CCV inoculum. The inoculum was prepared by diluting 2.5 μl of infected fluids from a confluent monolayer into 13.0 mls of media. One ml of this material was used to infect a roller bottle and the cells were grown until they demonstrated a pronounced cytopathic effect at 48 hours. The infected -monolayers were harvested and total cytoplasmic RNA was extracted using the guanidinium thiocyanate procedure as described in Chirgwin et al., *Biochem.*, 18:5294 (1979).

EXAMPLE 3

Primers Used for PCR Amplification of CCV Spike Gene Fragments

The primers appearing below in Table III were synthesized conventionally by the phosphoramidite method and gel purified prior to use. Primer #3045 was based on an FECV S gene sequence; and primers #4920, 1923, 2443 and 2600 were based on WT FIPV WSU 1146 sequences.

quoted from master mixes made with diethyl pyrocarbonate (DEPC) treated water and consisted of all of the reaction components except the RNA which was added last.

The mixture was incubated in a programmable thermal cycler [Perkin-Elmer Cetus, Norwalk, CT] at 21° C. for ten minutes followed by 42° C. for one hour then 95° C. for five minutes and finally held at 4° C. until PCR amplification.

Amplification of the cDNA was performed essentially according to the method of R. K. Saiki et al, *Science*, 230:1350–1354 (1985) using the Taq polymerase. Briefly, to the 20 μl cDNA reaction mix from above was added 10.0 μl 10X PCR buffer, 1.0 μl of each upstream and downstream primer previously diluted in water to 30 picomoles per microliter and 2.5 units of Taq polymerase (Perkin-Elmer Cetus, Norwalk, Conn.). Final volume was made up to 100 μl using DEPC treated water and overlaid with 100 μl of mineral oil. As above, master mixes were prepared to avoid contamination. The reaction was performed in the Perkin-Elmer Cetus thermal cycler for one cycle by denaturing at 95° C. for 1 minute, annealing at 37° C. for 3 minutes followed by an extension at 72° C. for 40 minutes. This initial cycle increased the likelihood of first strand DNA synthesis. A standard PCR profile was then performed by a 95° C. for 1 minute denaturation, 37° C. for 3 minutes annealing, 72° C. for 3 minutes extension for 40 cycles. A

TABLE III

| Amplified S Gene Region | Cloned Region | Top Primer | Bottom Primer |
|---|---|---|---|
| 1–362 aa | 1–352 aa | #3045 | #4920 |
| 352–1452 aa | 352–1452 aa | #2600 | #1923 |
| 1–555 aa | 128–555 aa | #3045 | #2443 |

| Primer # | DNA Sequence |
|---|---|
| 1923 [SEQ ID NO:46] | TAAAT<u>AGGCCT</u>TTAGTGGACATGCACTTTTTCAATTGG<br>     StuI |
| 2443 [SEQ ID NO:47] | TTAGT<u>AGGCCT</u>GTCGAGGCTATGGGTTGACCATAACCAC<br>     StuI |
| 2600 [SEQ ID NO:48] | CAGAT<u>CCCGGG</u>TGTACAATCTGGTATGGGTGCTACAG<br>     XmaI |
| 3045 [SEQ ID NO:49] | GTGCC<u>CCCGGG</u>TATGATTGTGCTCGTAACTTGCCTCTTG<br>     XmaI |
| 4920 [SEQ ID NO:50] | AGCACCCATACCAGATTGTACAT<u>CTGCAG</u>TGAAATTAAGATTG<br>                            PstI |

EXAMPLE 4

PCR Amplification of CCV S Gene

PCR amplified fragments of CCV S gene were generated using the following procedure. All PCR reagents were supplied by Perkin Elmer-Cetus, Norwalk, CT. In a final reaction volume of 20 μl of 1X RT buffer (5X RT buffer: 250 mM Tris-HCl, pH 8.3, 375 mM KCl, 15 mM MgCl$_2$), the following components were assembled in RNAse-free siliconized 500 μl microcentrifuge tubes: 1.0 mM of each dNTP, 20 units of RNAsin [Promega Corp, Madison, Wis.], 2.5 picomoles of random hexamer oligonucleotides [Pharmacia, Milwaukee, Wis.], 100 picomoles/μl solution in TE buffer (10 mM Tris-HCl, 1 mM EDTA, pH 7.5), 200 units of reverse transcriptase [Superscript RT, Bethesda Research Labs, Gaithersburg, MD] and 1.0 μg of respective RNA isolated as described above in Example 3. To avoid pipetting errors and contamination, all solutions were alifinal extension cycle was done by 95° C. for 1 minute denaturation, 37° C. for 2 minutes annealing, 72° C. for 15 minutes extension and held at 4° C. until analyzed.

PCR products were analyzed by electrophoresing 5.0 μl of the reaction on a 1.2% agarose gel for 16–17 hours. Bands were visualized by ethidium bromide staining the gel and fluorescence by UV irradiation at 256 nm. Photography using Polaroid type 55 film provided a negative that could be digitized for sample distance migration and comparison against markers run on each gel. The actual sizes of the bands were then calculated using the Beckman Microgenie software running on an IBM AT.

EXAMPLE 5

Cloning of CCV Spike Gene Regions

Cloning procedures were performed substantially as described by Maniatis et al, cited above. Details of the clonings are provided in the following examples. Calf-alkaline phosphatase was from Bethesda Research Labs (Gaithersburg, M. D.). Ligation products were transformed into E. coli host strain XL1 Blue [Stratagene Cloning Systems, La Jolla, Calif.]. pBluescript SK$_{II}$M13-phagemid vector was also obtained from Stratagene Cloning Systems. All restriction enzymes were purchased from New England Biolabs (Beverly, Mass.) or Bethesda Research Labs (Gaithersburg, Md.) and used according to manufacturer's specifications. T4 DNA ligase was received from Boehringer Mannheim Biochemicals (Indianapolis, Ind.). Calf intestinal alkaline phosphatase was purchased from Bethesda Research Labs.

EXAMPLE 6

CCV S Protein Fragment, A.A. 1–128 [SEQ ID NO: 51]

Five microliters (approximately 200 ng) of PCR-amplified DNA representing amino acids 1–362 [SEQ ID NO:53] of the CCV spike gene were ligated to the pT7Blue T-Vector (Novagen, Madison, Wis.) as per the manufacturer's instructions. One microliter of the ligation mix was used to transform NovaBlue competent cells (Novagen) and transformation mixes were plated on LB plates supplemented with ampicillin, isopropylthio-β-galactoside (IPTG; Sigma Chemical Co., St. Louis, Mo.), and 5-bromo-4-chloro-3-indolyl-β-D-galactoside (X-gal; Sigma Chemical Co., St. Louis, Mo.). White colonies were picked and screened by restriction analysis of mini-prep DNA. Insert-bearing clones were identified and oriented with respect to vector by SmaI/PstI, StuI, and PstI digests. Clone #2964 contained a full-length 1–362 amino acid insert and was used to provide sequence analysis from 1–128 amino acids of the CCV S gene.

EXAMPLE 7

CCV S Protein Fragment, A.A. 128–555 [SEQ ID NO:43]

10µl of PCR DNA encoding 1–555aa of the CCV spike protein was digested with SmaI/StuI for 4 hours at room temperature. DNA bands were isolated and purified from low-melting temperature agarose gels as described by Maniatis et al, cited above. Briefly, DNA fragments were visualized after staining with ethidium bromide, excised from the gel with a scalpel and transferred to microfuge tubes. Gel slices were incubated 5 min at 65° C., vortexed, and 5 volumes of 20 mM Tris, pH 8.0, 1 mM EDTA were added. Samples were incubated an additional 2 minutes at 65° C. and were then extracted once with phenol and again with phenol:chloroform. The DNA was precipitated with ¹⁄₁₀ volume 3 M NaOAc, pH 7.0, and 2.5 volumes of cold 95% EtOH overnight at −20° C. Insert DNAs were ligated to SK$_{II}$M13-SmaI-digested, dephosphorylated vector [Stratagene] for 4 hours at room temperature. Insert-bearing clones were identified by XhoI/SstI and BqlI digests of mini-prep DNA. Restriction enzyme and sequence analysis indicated that the cloned insert was short by −300bp due to the presence of a StuI site at amino acid #128 of the CCV spike gene. Therefore, these clones contained the CCV S protein spanning amino acids from about 128–555 [SEQ ID NO:43].

EXAMPLE 8

CCV S Protein Fragment, A.A. 352–1452 [SEQ ID NO:52]

PCR-amplified DNA fragments encoding amino acids 352–1454 of the CCV spike protein were purified using Prime-Erase Quik Columns [Stratagene] according to the manufacturer's instructions. Column-purified DNAs were then digested with XmaI/EcoRV overnight at 15° C. and subsequently isolated and eluted from low-melting temperature agarose gels as described by Maniatis et al, cited above. Inserts were ligated overnight at 15° C. to SK$_{II}$M13 XmaI/StuI digested, dephosphorylated vector [Stratagene]. Clones were identified and oriented with respect to vector by XhoI/SstI and PvuII digests of mini-prep DNAs, respectively.

EXAMPLE 9

DNA Sequencing

DNA sequence for the CCV S gene was determined from the individual clones #1775 (AA 352–1452; SEQ ID NO:52), #2007 (AA 128–555; SEQ ID NO:43) and #2964 (AA 1-362; SEQ ID NO:53). Nested set deletions were prepared from each clone or internal primers synthesized to facilitate primer walking and the sequence determined from both strands [Lark Sequencing Technologies, Houston, Tex]. The chain termination method performed as described in Sanger et al, *Proc. Natl. Acad. Sci. USA*, 74:5463–5467 (1977) was used to determine the sequence of all clones. The full length sequence of the CCV S gene was assembled from overlapping sequences of each of the three separate fragments by computer analysis.

DNA sequence analysis was performed using either Beckman Microgenie programs on an IBM Model PS/2 Model 70 or the University of Wisconsin GCG package of programs implemented on a DEC VAX cluster [Devereau et al., (1984)].

SEQ ID NO:1 is the complete nucleotide sequence of the CCV strain 1-71 S gene. The amino acid [SEQ ID NO:2] and nucleotide sequences [SEQ ID NO:1] of CCV 1-71 total 1452 amino acids and 4356 base pairs. CCV 1-71 has a DNA homology of 90.8% to published FIPV strain WT WSU 1146, 93.2% identity with FIPV strain DF2 and 94.1% similarity with FECV. In comparison to WSU 1146, this CCV strain further contains two amino acid deletions at positions 11 and 12, and two amino acid insertions at positions 118 and 119. In comparison to the amino acid sequences of other coronavirus S genes, the amino acid sequence of CCV is 82.2% homologous to TGEV, 89.7% homologous to DF2-HP, 90.0% homologous to TS-BP, 92.9% homologous to TS, 93.2% homologous to DF2, and 94.1% homologous to FECV.

The canine coronavirus S gene encoding amino acids #225–1325 [SEQ ID NO:54] has an overall homology to the published WT FIPV WSU 1146 strain at amino acids 352 to 1454 of 95.9%. The homology level is increased to 97.5% when the comparison is done under the amino acid similarity rules as proposed by M. O. Dayhoff, Atlas of Protein Sequence and Structure, Vol. 5, Supp. 3, Natl. Biomed. Res. Found., Washington, D.C. (1978). There are 42 amino acid diferences between the CCV S gene and the published sequence of WSU 1146 strain within the CCV sequence of SEQ ID NO: 2. Other CCV fragment homologies with WT FIPV WSU 1146 are illustrated in Table II above.

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. An isolated DNA molecule, comprising nucleotides 1 to 4356 of the S protein gene of canine coronavirus (CCV) strain 1-71 (SEQ ID NO:1).

2. An isolated DNA molecule, comprising:
   (a) nucleotides 1 to 4356 of the S protein gene of canine coronavirus (CCV) strain 1-71 (SEQ ID NO:1); or
   (b) a polynucleotide that encodes the protein encoded by (a).

3. An isolated recombinant DNA molecule from which a fusion protein can be expressed, said DNA molecule comprising:
   (a) a nucleotide sequence according to claim 2; and
   (b) a further polypeptide-encoding nucleotide sequence.

4. A recombinant DNA molecule comprising the polynucleotide of claim 2 in operative association with with one or more regulatory sequences capable of directing the expression of canine coronavirus (CCV) strain 1-71 S protein (SEQ ID NO:2) in a host.

5. A host cell comprising the recombinant DNA molecule of claim 4.

6. A host cell according to claim 5 that is a mammalian cell.

7. A method for the production of canine coronavirus (CCV) strain 1-71 S protein (SEQ ID NO:2) comprising culturing the transformed host cell of claim 5 under conditions wherein said protein is produced, and recovering said protein from the cell culture.

8. A host viral vector comprising the recombinant DNA molecule of claim 4.

9. A method for the production of canine coronavirus (CCV) strain 1-71 S protein (SEQ ID NO:2) comprising culturing a host viral vector of claim 8 under conditions wherein said protein is produced, and recovering said protein from the viral culture.

* * * * *

SEQUENCE LISTING (1) GENERAL INFORMATION:

(iii) NUMBER OF SEQUENCES: 59

(2) INFORMATION FOR SEQ ID NO:1:

(i) SEQUENCE CHARACTERISTICS:
      (A) LENGTH: 4359 base pairs
      (B) TYPE: nucleic acid
      (C) STRANDEDNESS: double
      (D) TOPOLOGY: unknown (ii) MOLECULE TYPE: DNA (genomic)

(ix) FEATURE:
      (A) NAME/KEY: CDS
      (B) LOCATION: 1..4356

(xi) SEQUENCE DESCRIPTION: SEQ ID NO:1:

```
ATG ATT GTG CTC GTA ACT TGC CTC TTG TTT TCG TAC AAT AGT GTG ATT       48
Met Ile Val Leu Val Thr Cys Leu Leu Phe Ser Tyr Asn Ser Val Ile
 1               5                  10                  15

TGT ACA TCA AAC AAT GAC TGT GTA CAA GTT AAT GTG ACA CAA TTG CCT       96
Cys Thr Ser Asn Asn Asp Cys Val Gln Val Asn Val Thr Gln Leu Pro
             20                  25                  30

GGC AAT GAA AAC ATT ATT AAA GAT TTT CTA TTT CAC ACC TTC AAA GAA      144
Gly Asn Glu Asn Ile Ile Lys Asp Phe Leu Phe His Thr Phe Lys Glu
         35                  40                  45

GAA GGA AGT GTA GTT GTT GGT GGT TAT TAC CCT ACA GAG GTG TGG TAT      192
Glu Gly Ser Val Val Val Gly Gly Tyr Tyr Pro Thr Glu Val Trp Tyr
     50                  55                  60

AAC TGC TCC AGA AGC GCA ACA ACC ACC GCT TAC AAG GAT TTT AGT AAT      240
Asn Cys Ser Arg Ser Ala Thr Thr Thr Ala Tyr Lys Asp Phe Ser Asn
 65                  70                  75                  80

ATA CAT GCA TTC TAT TTT GAT ATG GAA GCC ATG GAG AAT AGT ACT GGC      288
Ile His Ala Phe Tyr Phe Asp Met Glu Ala Met Glu Asn Ser Thr Gly
                 85                  90                  95

AAT GCA CGA GGT AAA CCT TTA CTA GTA CAT GTT CAT GGT GAT CCT GTT      336
Asn Ala Arg Gly Lys Pro Leu Leu Val His Val His Gly Asp Pro Val
            100                 105                 110

AGT ATC ATC ATA TAT ATA TCG GCT TAT AGA GAT GAT GTG CAA GGA AGG      384
Ser Ile Ile Ile Tyr Ile Ser Ala Tyr Arg Asp Asp Val Gln Gly Arg
        115                 120                 125

CCT CTT TTA AAA CAT GGT TTG TTG TGT ATA ACT AAA AAT AAA ATC ATT      432
Pro Leu Leu Lys His Gly Leu Leu Cys Ile Thr Lys Asn Lys Ile Ile
    130                 135                 140

GAC TAT AAC ACG TTT ACC AGC GCA CAG TGG AGT GCC ATA TGT TTG GGT      480
Asp Tyr Asn Thr Phe Thr Ser Ala Gln Trp Ser Ala Ile Cys Leu Gly
145                 150                 155                 160

GAT GAC AGA AAA ATA CCA TTC TCT GTC ATA CCC ACA GGT AAT GGT ACA      528
Asp Asp Arg Lys Ile Pro Phe Ser Val Ile Pro Thr Gly Asn Gly Thr
                165                 170                 175

AAA ATA TTT GGT CTT GAG TGG AAT GAT GAC TAT GTT ACA GCC TAT ATT      576
Lys Ile Phe Gly Leu Glu Trp Asn Asp Asp Tyr Val Thr Ala Tyr Ile
            180                 185                 190

AGT GAT CGT TCT CAC CAT TTG AAC ATC AAT AAT AAT TGG TTT AAC AAT      624
Ser Asp Arg Ser His His Leu Asn Ile Asn Asn Asn Trp Phe Asn Asn
        195                 200                 205

GTG ACA ATC CTA TAC TCT CGA TCA AGC ACT GCT ACG TGG CAG AAG AGT      672
Val Thr Ile Leu Tyr Ser Arg Ser Ser Thr Ala Thr Trp Gln Lys Ser
    210                 215                 220
```

```
GCT GCA TAT GTT TAT CAA GGT GTT TCA AAT TTT ACT TAT TAC AAG TTA    720
Ala Ala Tyr Val Tyr Gln Gly Val Ser Asn Phe Thr Tyr Tyr Lys Leu
225             230                 235                 240

AAT AAC ACC AAT GGC TTG AAA AGC TAT GAA TTG TGT GAA GAT TAT GAA    768
Asn Asn Thr Asn Gly Leu Lys Ser Tyr Glu Leu Cys Glu Asp Tyr Glu
                245                 250                 255

TGC TGC ACT GGC TAT GCT ACC AAC GTA TTT GCC CCG ACA GTG GGC GGT    816
Cys Cys Thr Gly Tyr Ala Thr Asn Val Phe Ala Pro Thr Val Gly Gly
            260                 265                 270

TAT ATA CCT GAT GGC TTC AGT TTT AAC AAT TGG TTT ATG CTT ACA AAC    864
Tyr Ile Pro Asp Gly Phe Ser Phe Asn Asn Trp Phe Met Leu Thr Asn
        275                 280                 285

AGT TCC ACG TTT GTT AGT GGC AGA TTT GTA ACA AAT CAA CCA TTA TTG    912
Ser Ser Thr Phe Val Ser Gly Arg Phe Val Thr Asn Gln Pro Leu Leu
    290                 295                 300

GTT AAT TGT TTG TGG CCA GTG CCC AGT CTT GGT GTC GCA GCA CAA GAA    960
Val Asn Cys Leu Trp Pro Val Pro Ser Leu Gly Val Ala Ala Gln Glu
305                 310                 315                 320

TTT TGT TTT GAA GGT GCG CAG TTT AGC CAA TGT AAT GGT GTG TCT TTA   1008
Phe Cys Phe Glu Gly Ala Gln Phe Ser Gln Cys Asn Gly Val Ser Leu
                325                 330                 335

AAC AAT ACA GTG GAT GTC ATT AGA TTC AAC CTT AAT TTT ACC ACA GAT   1056
Asn Asn Thr Val Asp Val Ile Arg Phe Asn Leu Asn Phe Thr Thr Asp
                340                 345                 350

GTA CAA TCT GGT ATG GGT GCT ACA GTA TTT TCA CTG AAT ACA ACA GGT   1104
Val Gln Ser Gly Met Gly Ala Thr Val Phe Ser Leu Asn Thr Thr Gly
            355                 360                 365

GGT GTC ATT CTT GAG ATT TCT TGT TAT AAT GAT ACA GTG AGT GAG TCA   1152
Gly Val Ile Leu Glu Ile Ser Cys Tyr Asn Asp Thr Val Ser Glu Ser
        370                 375                 380

AGT TTC TAC AGT TAT GGT GAA ATT TCA TTC GGC GTA ACT GAT GGA CCG   1200
Ser Phe Tyr Ser Tyr Gly Glu Ile Ser Phe Gly Val Thr Asp Gly Pro
385                 390                 395                 400

CGT TAC TGT TAC GCA CTC TAT AAT GGC ACG GCT CTT AAG TAT TTA GGA   1248
Arg Tyr Cys Tyr Ala Leu Tyr Asn Gly Thr Ala Leu Lys Tyr Leu Gly
                405                 410                 415

ACA TTA CCA CCT AGT GTC AAG GAA ATT GCT ATT AGT AAG TGG GGC CAT   1296
Thr Leu Pro Pro Ser Val Lys Glu Ile Ala Ile Ser Lys Trp Gly His
                420                 425                 430

TTT TAT ATT AAT GGT TAC AAT TTC TTT AGC ACT TTT CCT ATT GAT TGT   1344
Phe Tyr Ile Asn Gly Tyr Asn Phe Phe Ser Thr Phe Pro Ile Asp Cys
            435                 440                 445

ATA TCT TTT AAT TTA ACC ACT GGT GAT AGT GGA GCA TTT TGG ACA ATT   1392
Ile Ser Phe Asn Leu Thr Thr Gly Asp Ser Gly Ala Phe Trp Thr Ile
        450                 455                 460

GCT TAC ACA TCG TAC ACT GAC GCA TTA GTA CAA GTT GAA AAC ACA GCT   1440
Ala Tyr Thr Ser Tyr Thr Asp Ala Leu Val Gln Val Glu Asn Thr Ala
465                 470                 475                 480

ATT AAA AAG GTG ACG TAT TGT AAC AGT CAC ATT AAT AAC ATT AAA TGT   1488
Ile Lys Lys Val Thr Tyr Cys Asn Ser His Ile Asn Asn Ile Lys Cys
                485                 490                 495

TCT CAA CTT ACT GCT AAT TTG CAA AAT GGA TTT TAT CCT GTT GCT TCA   1536
Ser Gln Leu Thr Ala Asn Leu Gln Asn Gly Phe Tyr Pro Val Ala Ser
                500                 505                 510

AGT GAA GTT GGT CTT GTC AAT AAG AGT GTT GTG TTA CTA CCT AGT TTC   1584
Ser Glu Val Gly Leu Val Asn Lys Ser Val Val Leu Leu Pro Ser Phe
            515                 520                 525

TAT TCA CAT ACC AGT GTT AAT ATA ACT ATT GAT CTT GGT ATG AAG CGT   1632
Tyr Ser His Thr Ser Val Asn Ile Thr Ile Asp Leu Gly Met Lys Arg
```

```
                530                 535                 540
AGT GGT TAT GGT CAA CCC ATA GCC TCA ACA TTA AGT AAC ATC ACA CTA        1680
Ser Gly Tyr Gly Gln Pro Ile Ala Ser Thr Leu Ser Asn Ile Thr Leu
545                 550                 555                 560

CCA ATG CAG GAT AAT AAC ACC GAT GTG TAC TGC ATT CGT TCT AAC CAA        1728
Pro Met Gln Asp Asn Asn Thr Asp Val Tyr Cys Ile Arg Ser Asn Gln
                565                 570                 575

TTT TCA GTT TAC GTT CAT TCC ACT TGT AAA AGT TCT TTA TGG GAC GAT        1776
Phe Ser Val Tyr Val His Ser Thr Cys Lys Ser Ser Leu Trp Asp Asp
                580                 585                 590

GTG TTT AAT TCC GAC TGC ACA GAT GTT TTA TAT GCT ACA GCT GTT ATA        1824
Val Phe Asn Ser Asp Cys Thr Asp Val Leu Tyr Ala Thr Ala Val Ile
                595                 600                 605

AAA ACT GGT ACT TGT CCT TTC TCG TTT GAT AAA TTG AAC AAT TAC TTA        1872
Lys Thr Gly Thr Cys Pro Phe Ser Phe Asp Lys Leu Asn Asn Tyr Leu
610                 615                 620

ACT TTT AAC AAG TTC TGT TTG TCA TTG AAT CCT GTT GGT GCC AAC TGC        1920
Thr Phe Asn Lys Phe Cys Leu Ser Leu Asn Pro Val Gly Ala Asn Cys
625                 630                 635                 640

AAG TTT GAT GTT GCC GCT CGT ACA AGA ACC AAT GAG CAG GTT GTT AGA        1968
Lys Phe Asp Val Ala Ala Arg Thr Arg Thr Asn Glu Gln Val Val Arg
                645                 650                 655

AGT TTA TAT GTA ATA TAT GAA GAA GGA GAC AAC ATA GTG GGT GTG CCG        2016
Ser Leu Tyr Val Ile Tyr Glu Glu Gly Asp Asn Ile Val Gly Val Pro
                660                 665                 670

TCT GAC AAT AGT GGT CTT CAC GAC TTG TCA GTG CTA CAC TTA GAC TCC        2064
Ser Asp Asn Ser Gly Leu His Asp Leu Ser Val Leu His Leu Asp Ser
                675                 680                 685

TGT ACA GAT TAT AAT ATA TAT GGT AGA ACT GGT GTT GGT ATT ATT AGA        2112
Cys Thr Asp Tyr Asn Ile Tyr Gly Arg Thr Gly Val Gly Ile Ile Arg
690                 695                 700

CAA ACT AAC AGT ACG CTA CTT AGT GGC TTA TAT TAC ACA TCA CTA TCA        2160
Gln Thr Asn Ser Thr Leu Leu Ser Gly Leu Tyr Tyr Thr Ser Leu Ser
705                 710                 715                 720

GGT GAC TTG TTA GGG TTT AAA AAT GTT AGT GAT GGT GTC ATC TAT TCT        2208
Gly Asp Leu Leu Gly Phe Lys Asn Val Ser Asp Gly Val Ile Tyr Ser
                725                 730                 735

GTC ACG CCA TGT GAT GTA AGC GCA CAA GCT GCT GTT ATT GAT GGC GCC        2256
Val Thr Pro Cys Asp Val Ser Ala Gln Ala Ala Val Ile Asp Gly Ala
                740                 745                 750

ATA GTT GGA GCT ATG ACT TCC ATT AAT AGT GAA ATG TTA GGT CTA ACA        2304
Ile Val Gly Ala Met Thr Ser Ile Asn Ser Glu Met Leu Gly Leu Thr
                755                 760                 765

CAT TGG ACA ACA ACA CCT AAT TTT TAT TAT TAT TCT ATA TAT AAT TAT        2352
His Trp Thr Thr Thr Pro Asn Phe Tyr Tyr Tyr Ser Ile Tyr Asn Tyr
770                 775                 780

ACC AAT GAA AGG ACT CGT GGC ACA GCA ATT GAT AGT AAC GAT GTT GAT        2400
Thr Asn Glu Arg Thr Arg Gly Thr Ala Ile Asp Ser Asn Asp Val Asp
785                 790                 795                 800

TGT GAA CCT ATC ATA ACC TAT TCT AAT ATA GGT GTT TGT AAA AAT GGA        2448
Cys Glu Pro Ile Ile Thr Tyr Ser Asn Ile Gly Val Cys Lys Asn Gly
                805                 810                 815

GCT TTG GTT TTT ATT AAC GTC ACA CAT TCT GAT GGA GAC GTT CAA CCA        2496
Ala Leu Val Phe Ile Asn Val Thr His Ser Asp Gly Asp Val Gln Pro
                820                 825                 830

ATT AGC ACC GGT AAT GTC ACG ATA CCT ACA AAT TTT ACC ATA TCT GTG        2544
Ile Ser Thr Gly Asn Val Thr Ile Pro Thr Asn Phe Thr Ile Ser Val
                835                 840                 845

CAA GTT GAG TAC ATT CAG GTT TAC ACT ACA CCG GTG TCA ATA GAT TGT        2592
```

```
                        -continued

Gln Val Glu Tyr Ile Gln Val Tyr Thr Thr Pro Val Ser Ile Asp Cys
    850                 855                 860

TCA AGG TAC GTT TGC AAT GGT AAC CCT AGA TGC AAT AAA TTG TTA ACG       2640
Ser Arg Tyr Val Cys Asn Gly Asn Pro Arg Cys Asn Lys Leu Leu Thr
865                 870                 875                 880

CAA TAC GTT TCT GCA TGT CAA ACT ATT GAG CAA GCA CTT GCA ATG GGT       2688
Gln Tyr Val Ser Ala Cys Gln Thr Ile Glu Gln Ala Leu Ala Met Gly
                    885                 890                 895

GCC AGA CTT GAA AAC ATG GAG ATT GAT TCC ATG TTG TTT GTT TCG GAA       2736
Ala Arg Leu Glu Asn Met Glu Ile Asp Ser Met Leu Phe Val Ser Glu
                900                 905                 910

AAT GCC CTT AAA TTG GCA TCT GTT GAA GCA TTC AAT AGT ACG GAA ACT       2784
Asn Ala Leu Lys Leu Ala Ser Val Glu Ala Phe Asn Ser Thr Glu Thr
            915                 920                 925

TTA GAT CCT ATT TAC AAA GAA TGG CCT AAC ATT GGT GGT TCT TGG CTA       2832
Leu Asp Pro Ile Tyr Lys Glu Trp Pro Asn Ile Gly Gly Ser Trp Leu
        930                 935                 940

GGA GGT TTA AAA GAC ATA TTG CCA TCT CAC AAC AGC AAA CGT AAG TAC       2880
Gly Gly Leu Lys Asp Ile Leu Pro Ser His Asn Ser Lys Arg Lys Tyr
945                 950                 955                 960

CGG TCG GCT ATA GAA GAT TTG CTT TTT GAT AAG GTT GTA ACA TCT GGC       2928
Arg Ser Ala Ile Glu Asp Leu Leu Phe Asp Lys Val Val Thr Ser Gly
                    965                 970                 975

TTA GGT ACA GTT GAT GAA GAT TAT AAA CGT TGT ACA GGT GGT TAT GAC       2976
Leu Gly Thr Val Asp Glu Asp Tyr Lys Arg Cys Thr Gly Gly Tyr Asp
                980                 985                 990

ATA GCT GAC TTA GTG TGT GCA CAA TAT TAC AAT GGC ATC ATG GTG CTA       3024
Ile Ala Asp Leu Val Cys Ala Gln Tyr Tyr Asn Gly Ile Met Val Leu
            995                 1000                1005

CCT GGT GTA GCT AAT GAT GAC AAG ATG GCT ATG TAC ACT GCA TCT CTT       3072
Pro Gly Val Ala Asn Asp Asp Lys Met Ala Met Tyr Thr Ala Ser Leu
        1010                1015                1020

GCA GGT GGT ATA ACA TTA GGT GCA CTT GGT GGT GGC GCA GTG TCT ATA       3120
Ala Gly Gly Ile Thr Leu Gly Ala Leu Gly Gly Gly Ala Val Ser Ile
1025                1030                1035                1040

CCT TTT GCA ATA GCA GTT CAA GCC AGA CTT AAT TAT GTT GCT CTA CAA       3168
Pro Phe Ala Ile Ala Val Gln Ala Arg Leu Asn Tyr Val Ala Leu Gln
                    1045                1050                1055

ACT GAT GTA TTG AGC AAG AAC CAG CAG ATC CTG GCT AAT GCT TTC AAT       3216
Thr Asp Val Leu Ser Lys Asn Gln Gln Ile Leu Ala Asn Ala Phe Asn
                1060                1065                1070

CAA GCT ATT GGT AAC ATT ACA CAG GCA TTT GGT AAG GTT AAT GAT GCT       3264
Gln Ala Ile Gly Asn Ile Thr Gln Ala Phe Gly Lys Val Asn Asp Ala
            1075                1080                1085

ATA CAT CAA ACG TCA CAA GGT CTT GCT ACT GTT GCT AAA GCA TTG GCA       3312
Ile His Gln Thr Ser Gln Gly Leu Ala Thr Val Ala Lys Ala Leu Ala
        1090                1095                1100

AAA GTG CAA GAT GTT GTT AAC ACA CAA GGG CAA GCT TTA AGC CAC CTA       3360
Lys Val Gln Asp Val Val Asn Thr Gln Gly Gln Ala Leu Ser His Leu
1105                1110                1115                1120

ACA GTA CAA TTG CAA AAT AAT TTC CAA GCC ATT AGT AGT TCC ATT AGT       3408
Thr Val Gln Leu Gln Asn Asn Phe Gln Ala Ile Ser Ser Ser Ile Ser
                    1125                1130                1135

GAC ATT TAT AAC AGG CTT GAT GAA TTG AGT GCT GAT GCA CAA GTT GAC       3456
Asp Ile Tyr Asn Arg Leu Asp Glu Leu Ser Ala Asp Ala Gln Val Asp
                1140                1145                1150

AGG CTG ATT ACA GGA AGA CTT ACA GCA CTT AAT GCA TTT GTG TCT CAG       3504
Arg Leu Ile Thr Gly Arg Leu Thr Ala Leu Asn Ala Phe Val Ser Gln
            1155                1160                1165
```

```
ACT TTA ACC AGA CAA GCA GAG GTT AGG GCT AGC AGA CAG CTT GCT AAA         3552
Thr Leu Thr Arg Gln Ala Glu Val Arg Ala Ser Arg Gln Leu Ala Lys
        1170                1175                1180

GAC AAG GTA AAT GAA TGC GTT AGG TCT CAA TCT CAG AGA TTT GGA TTC         3600
Asp Lys Val Asn Glu Cys Val Arg Ser Gln Ser Gln Arg Phe Gly Phe
1185                1190                1195                1200

TGT GGT AAT GGT ACA CAT TTA TTT TCA CTT GCA AAT GCA GCA CCA AAT         3648
Cys Gly Asn Gly Thr His Leu Phe Ser Leu Ala Asn Ala Ala Pro Asn
            1205                1210                1215

GGC ATG ATC TTC TTT CAC ACA GTG CTA TTA CCA ACA GCT TAT GAA ACC         3696
Gly Met Ile Phe Phe His Thr Val Leu Leu Pro Thr Ala Tyr Glu Thr
                1220                1225                1230

GTG ACG GCC TGG TCA GGT ATT TGT GCA TCA GAT GGC GAT CGT ACT TTT         3744
Val Thr Ala Trp Ser Gly Ile Cys Ala Ser Asp Gly Asp Arg Thr Phe
            1235                1240                1245

GGA CTT GTT GTT AAG GAT GTC CAG TTG ACG CTG TTT CGC AAT CTA GAT         3792
Gly Leu Val Val Lys Asp Val Gln Leu Thr Leu Phe Arg Asn Leu Asp
        1250                1255                1260

GAC AAA TTC TAT TTG ACT CCC AGA ACT ATG TAT CAG CCT AGA GTT GCA         3840
Asp Lys Phe Tyr Leu Thr Pro Arg Thr Met Tyr Gln Pro Arg Val Ala
1265                1270                1275                1280

ACT AGT TCT GAT TTT GTT CAA ATT GAA GGA TGT GAT GTG TTG TTT GTT         3888
Thr Ser Ser Asp Phe Val Gln Ile Glu Gly Cys Asp Val Leu Phe Val
            1285                1290                1295

AAT GCA ACT GTA ATT GAC TTG CCT AGT ATT ATA CCT GAC TAT ATT GAT         3936
Asn Ala Thr Val Ile Asp Leu Pro Ser Ile Ile Pro Asp Tyr Ile Asp
                1300                1305                1310

ATT AAT CAA ACT GTT CAG GAC ATA TTA GAA AAT TTC AGA CCA AAT TGG         3984
Ile Asn Gln Thr Val Gln Asp Ile Leu Glu Asn Phe Arg Pro Asn Trp
            1315                1320                1325

ACT GTA CCT GAG TTG CCA CTT GAC ATT TTC AAT GCA ACC TAC TTA AAC         4032
Thr Val Pro Glu Leu Pro Leu Asp Ile Phe Asn Ala Thr Tyr Leu Asn
        1330                1335                1340

CTG ACT GGT GAA ATT AAT GAC TTA GAA TTT AGG TCA GAA AAG TTA CAT         4080
Leu Thr Gly Glu Ile Asn Asp Leu Glu Phe Arg Ser Glu Lys Leu His
1345                1350                1355                1360

AAC ACC ACA GTA GAA CTT GCT ATT CTC ATT GAT AAT ATT AAT AAC ACA         4128
Asn Thr Thr Val Glu Leu Ala Ile Leu Ile Asp Asn Ile Asn Asn Thr
            1365                1370                1375

TTA GTC AAT CTT GAA TGG CTC AAT AGA ATT GAA ACT TAT GTA AAA TGG         4176
Leu Val Asn Leu Glu Trp Leu Asn Arg Ile Glu Thr Tyr Val Lys Trp
                1380                1385                1390

CCT TGG TAT GTG TGG CTA CTA ATT GGA TTA GTA GTA ATA TTC TGC ATA         4224
Pro Trp Tyr Val Trp Leu Leu Ile Gly Leu Val Val Ile Phe Cys Ile
            1395                1400                1405

CCC ATA TTG CTA TTT TGT TGT TGT AGC ACT GGT TGT TGT GGA TGT ATT         4272
Pro Ile Leu Leu Phe Cys Cys Cys Ser Thr Gly Cys Cys Gly Cys Ile
        1410                1415                1420

GGG TGT TTA GGA AGC TGT TGT CAT TCC ATA TGT AGT AGA AGG CGA TTT         4320
Gly Cys Leu Gly Ser Cys Cys His Ser Ile Cys Ser Arg Arg Arg Phe
1425                1430                1435                1440

GAA AGT TAT GAA CCA ATT GAA AAA GTG CAT GTC CAC TAA                     4359
Glu Ser Tyr Glu Pro Ile Glu Lys Val His Val His
            1445                1450
```

(2) INFORMATION FOR SEQ ID NO:2:

(i) SEQUENCE CHARACTERISTICS:
        (A) LENGTH: 1452 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ile Val Leu Val Thr Cys Leu Leu Phe Ser Tyr Asn Ser Val Ile
 1               5                  10                  15

Cys Thr Ser Asn Asn Asp Cys Val Gln Val Asn Val Thr Gln Leu Pro
                20                  25                  30

Gly Asn Glu Asn Ile Ile Lys Asp Phe Leu Phe His Thr Phe Lys Glu
                35                  40                  45

Glu Gly Ser Val Val Val Gly Gly Tyr Tyr Pro Thr Glu Val Trp Tyr
        50                  55                  60

Asn Cys Ser Arg Ser Ala Thr Thr Ala Tyr Lys Asp Phe Ser Asn
 65                  70                  75                  80

Ile His Ala Phe Tyr Phe Asp Met Glu Ala Met Glu Asn Ser Thr Gly
                    85                  90                  95

Asn Ala Arg Gly Lys Pro Leu Leu Val His Val His Gly Asp Pro Val
                100                 105                 110

Ser Ile Ile Ile Tyr Ile Ser Ala Tyr Arg Asp Asp Val Gln Gly Arg
                115                 120                 125

Pro Leu Leu Lys His Gly Leu Leu Cys Ile Thr Lys Asn Lys Ile Ile
130                 135                 140

Asp Tyr Asn Thr Phe Thr Ser Ala Gln Trp Ser Ala Ile Cys Leu Gly
145                 150                 155                 160

Asp Asp Arg Lys Ile Pro Phe Ser Val Ile Pro Thr Gly Asn Gly Thr
                165                 170                 175

Lys Ile Phe Gly Leu Glu Trp Asn Asp Asp Tyr Val Thr Ala Tyr Ile
                180                 185                 190

Ser Asp Arg Ser His His Leu Asn Ile Asn Asn Asn Trp Phe Asn Asn
                195                 200                 205

Val Thr Ile Leu Tyr Ser Arg Ser Ser Thr Ala Thr Trp Gln Lys Ser
                210                 215                 220

Ala Ala Tyr Val Tyr Gln Gly Val Ser Asn Phe Thr Tyr Tyr Lys Leu
225                 230                 235                 240

Asn Asn Thr Asn Gly Leu Lys Ser Tyr Glu Leu Cys Glu Asp Tyr Glu
                245                 250                 255

Cys Cys Thr Gly Tyr Ala Thr Asn Val Phe Ala Pro Thr Val Gly Gly
                260                 265                 270

Tyr Ile Pro Asp Gly Phe Ser Phe Asn Asn Trp Phe Met Leu Thr Asn
                275                 280                 285

Ser Ser Thr Phe Val Ser Gly Arg Phe Val Thr Asn Gln Pro Leu Leu
                290                 295                 300

Val Asn Cys Leu Trp Pro Val Pro Ser Leu Gly Val Ala Ala Gln Glu
305                 310                 315                 320

Phe Cys Phe Glu Gly Ala Gln Phe Ser Gln Cys Asn Gly Val Ser Leu
                325                 330                 335

Asn Asn Thr Val Asp Val Ile Arg Phe Asn Leu Asn Phe Thr Thr Asp
                340                 345                 350

Val Gln Ser Gly Met Gly Ala Thr Val Phe Ser Leu Asn Thr Thr Gly
                355                 360                 365

Gly Val Ile Leu Glu Ile Ser Cys Tyr Asn Asp Thr Val Ser Glu Ser
                370                 375                 380

Ser Phe Tyr Ser Tyr Gly Glu Ile Ser Phe Gly Val Thr Asp Gly Pro
385                 390                 395                 400
```

```
Arg Tyr Cys Tyr Ala Leu Tyr Asn Gly Thr Ala Leu Lys Tyr Leu Gly
                405                 410                 415
Thr Leu Pro Pro Ser Val Lys Glu Ile Ala Ile Ser Lys Trp Gly His
            420                 425                 430
Phe Tyr Ile Asn Gly Tyr Asn Phe Phe Ser Thr Phe Pro Ile Asp Cys
            435                 440                 445
Ile Ser Phe Asn Leu Thr Thr Gly Asp Ser Gly Ala Phe Trp Thr Ile
            450                 455                 460
Ala Tyr Thr Ser Tyr Thr Asp Ala Leu Val Gln Val Glu Asn Thr Ala
465                 470                 475                 480
Ile Lys Lys Val Thr Tyr Cys Asn Ser His Ile Asn Asn Ile Lys Cys
                485                 490                 495
Ser Gln Leu Thr Ala Asn Leu Gln Asn Gly Phe Tyr Pro Val Ala Ser
                500                 505                 510
Ser Glu Val Gly Leu Val Asn Lys Ser Val Val Leu Leu Pro Ser Phe
                515                 520                 525
Tyr Ser His Thr Ser Val Asn Ile Thr Ile Asp Leu Gly Met Lys Arg
                530                 535                 540
Ser Gly Tyr Gly Gln Pro Ile Ala Ser Thr Leu Ser Asn Ile Thr Leu
545                 550                 555                 560
Pro Met Gln Asp Asn Asn Thr Asp Val Tyr Cys Ile Arg Ser Asn Gln
                565                 570                 575
Phe Ser Val Tyr Val His Ser Thr Cys Lys Ser Ser Leu Trp Asp Asp
                580                 585                 590
Val Phe Asn Ser Asp Cys Thr Asp Val Leu Tyr Ala Thr Ala Val Ile
                595                 600                 605
Lys Thr Gly Thr Cys Pro Phe Ser Phe Asp Lys Leu Asn Asn Tyr Leu
                610                 615                 620
Thr Phe Asn Lys Phe Cys Leu Ser Leu Asn Pro Val Gly Ala Asn Cys
625                 630                 635                 640
Lys Phe Asp Val Ala Ala Arg Thr Arg Thr Asn Glu Gln Val Val Arg
                645                 650                 655
Ser Leu Tyr Val Ile Tyr Glu Glu Gly Asp Asn Ile Val Gly Val Pro
                660                 665                 670
Ser Asp Asn Ser Gly Leu His Asp Leu Ser Val Leu His Leu Asp Ser
                675                 680                 685
Cys Thr Asp Tyr Asn Ile Tyr Gly Arg Thr Gly Val Gly Ile Ile Arg
                690                 695                 700
Gln Thr Asn Ser Thr Leu Leu Ser Gly Leu Tyr Tyr Thr Ser Leu Ser
705                 710                 715                 720
Gly Asp Leu Leu Gly Phe Lys Asn Val Ser Asp Gly Val Ile Tyr Ser
                725                 730                 735
Val Thr Pro Cys Asp Val Ser Ala Gln Ala Ala Val Ile Asp Gly Ala
                740                 745                 750
Ile Val Gly Ala Met Thr Ser Ile Asn Ser Glu Met Leu Gly Leu Thr
                755                 760                 765
His Trp Thr Thr Thr Pro Asn Phe Tyr Tyr Ser Ile Tyr Asn Tyr
                770                 775                 780
Thr Asn Glu Arg Thr Arg Gly Thr Ala Ile Asp Ser Asn Asp Val Asp
785                 790                 795                 800
Cys Glu Pro Ile Ile Thr Tyr Ser Asn Ile Gly Val Cys Lys Asn Gly
                805                 810                 815
```

-continued

```
Ala Leu Val Phe Ile Asn Val Thr His Ser Asp Gly Asp Val Gln Pro
                820                 825                 830

Ile Ser Thr Gly Asn Val Thr Ile Pro Thr Asn Phe Thr Ile Ser Val
            835                 840                 845

Gln Val Glu Tyr Ile Gln Val Tyr Thr Thr Pro Val Ser Ile Asp Cys
        850                 855                 860

Ser Arg Tyr Val Cys Asn Gly Asn Pro Arg Cys Asn Lys Leu Leu Thr
865                 870                 875                 880

Gln Tyr Val Ser Ala Cys Gln Thr Ile Glu Gln Ala Leu Ala Met Gly
                885                 890                 895

Ala Arg Leu Glu Asn Met Glu Ile Asp Ser Met Leu Phe Val Ser Glu
            900                 905                 910

Asn Ala Leu Lys Leu Ala Ser Val Glu Ala Phe Asn Ser Thr Glu Thr
        915                 920                 925

Leu Asp Pro Ile Tyr Lys Glu Trp Pro Asn Ile Gly Gly Ser Trp Leu
    930                 935                 940

Gly Gly Leu Lys Asp Ile Leu Pro Ser His Asn Ser Lys Arg Lys Tyr
945                 950                 955                 960

Arg Ser Ala Ile Glu Asp Leu Leu Phe Asp Lys Val Val Thr Ser Gly
                965                 970                 975

Leu Gly Thr Val Asp Glu Asp Tyr Lys Arg Cys Thr Gly Gly Tyr Asp
            980                 985                 990

Ile Ala Asp Leu Val Cys Ala Gln Tyr Tyr Asn Gly Ile Met Val Leu
        995                 1000                1005

Pro Gly Val Ala Asn Asp Asp Lys Met Ala Met Tyr Thr Ala Ser Leu
    1010                1015                1020

Ala Gly Gly Ile Thr Leu Gly Ala Leu Gly Gly Gly Ala Val Ser Ile
1025                1030                1035                1040

Pro Phe Ala Ile Ala Val Gln Ala Arg Leu Asn Tyr Val Ala Leu Gln
                1045                1050                1055

Thr Asp Val Leu Ser Lys Asn Gln Gln Ile Leu Ala Asn Ala Phe Asn
            1060                1065                1070

Gln Ala Ile Gly Asn Ile Thr Gln Ala Phe Gly Lys Val Asn Asp Ala
        1075                1080                1085

Ile His Gln Thr Ser Gln Gly Leu Ala Thr Val Ala Lys Ala Leu Ala
    1090                1095                1100

Lys Val Gln Asp Val Val Asn Thr Gln Gly Gln Ala Leu Ser His Leu
1105                1110                1115                1120

Thr Val Gln Leu Gln Asn Asn Phe Gln Ala Ile Ser Ser Ser Ile Ser
                1125                1130                1135

Asp Ile Tyr Asn Arg Leu Asp Glu Leu Ser Ala Asp Ala Gln Val Asp
            1140                1145                1150

Arg Leu Ile Thr Gly Arg Leu Thr Ala Leu Asn Ala Phe Val Ser Gln
        1155                1160                1165

Thr Leu Thr Arg Gln Ala Glu Val Arg Ala Ser Arg Gln Leu Ala Lys
    1170                1175                1180

Asp Lys Val Asn Glu Cys Val Arg Ser Gln Ser Gln Arg Phe Gly Phe
1185                1190                1195                1200

Cys Gly Asn Gly Thr His Leu Phe Ser Leu Ala Asn Ala Ala Pro Asn
                1205                1210                1215

Gly Met Ile Phe Phe His Thr Val Leu Leu Pro Thr Ala Tyr Glu Thr
            1220                1225                1230

Val Thr Ala Trp Ser Gly Ile Cys Ala Ser Asp Gly Asp Arg Thr Phe
```

-continued

```
                    1235                1240                    1245

Gly Leu Val Val Lys Asp Val Gln Leu Thr Leu Phe Arg Asn Leu Asp
                    1250                1255                1260

Asp Lys Phe Tyr Leu Thr Pro Arg Thr Met Tyr Gln Pro Arg Val Ala
1265                1270                1275                1280

Thr Ser Ser Asp Phe Val Gln Ile Glu Gly Cys Asp Val Leu Phe Val
                    1285                1290                1295

Asn Ala Thr Val Ile Asp Leu Pro Ser Ile Ile Pro Asp Tyr Ile Asp
                    1300                1305                1310

Ile Asn Gln Thr Val Gln Asp Ile Leu Glu Asn Phe Arg Pro Asn Trp
                    1315                1320                1325

Thr Val Pro Glu Leu Pro Leu Asp Ile Phe Asn Ala Thr Tyr Leu Asn
                    1330                1335                1340

Leu Thr Gly Glu Ile Asn Asp Leu Glu Phe Arg Ser Glu Lys Leu His
1345                1350                1355                1360

Asn Thr Thr Val Glu Leu Ala Ile Leu Ile Asp Asn Ile Asn Asn Thr
                    1365                1370                1375

Leu Val Asn Leu Glu Trp Leu Asn Arg Ile Glu Thr Tyr Val Lys Trp
                    1380                1385                1390

Pro Trp Tyr Val Trp Leu Leu Ile Gly Leu Val Val Ile Phe Cys Ile
                    1395                1400                1405

Pro Ile Leu Leu Phe Cys Cys Cys Ser Thr Gly Cys Cys Gly Cys Ile
                    1410                1415                1420

Gly Cys Leu Gly Ser Cys Cys His Ser Ile Cys Ser Arg Arg Arg Phe
1425                1430                1435                1440

Glu Ser Tyr Glu Pro Ile Glu Lys Val His Val His
                    1445                1450

(2) INFORMATION FOR SEQ ID NO:3:

(i) SEQUENCE CHARACTERISTICS:
        (A) LENGTH: 201 amino acids
        (B) TYPE: amino acid
        (D) TOPOLOGY: unknown (ii) MOLECULE TYPE: protein (xi) SEQUENCE DESCRIPTION: SEQ ID NO:3:

Gly Ser Val Val Gly Gly Tyr Tyr Pro Thr Glu Val Trp Tyr Asn
1               5                   10                  15

Cys Ser Arg Ser Ala Thr Thr Ala Tyr Lys Asp Phe Ser Asn Ile
                20                  25                  30

His Ala Phe Tyr Phe Asp Met Glu Ala Met Glu Asn Ser Thr Gly Asn
                35                  40                  45

Ala Arg Gly Lys Pro Leu Leu Val His Val His Gly Asp Pro Val Ser
50                  55                  60

Ile Ile Ile Tyr Ile Ser Ala Tyr Arg Asp Asp Val Gln Gly Arg Pro
65                  70                  75                  80

Leu Leu Lys His Gly Leu Leu Cys Ile Thr Lys Asn Lys Ile Ile Asp
                85                  90                  95

Tyr Asn Thr Phe Thr Ser Ala Gln Trp Ser Ala Ile Cys Leu Gly Asp
                100                 105                 110

Asp Arg Lys Ile Pro Phe Ser Val Ile Pro Thr Gly Asn Gly Thr Lys
                115                 120                 125

Ile Phe Gly Leu Glu Trp Asn Asp Asp Tyr Val Thr Ala Tyr Ile Ser
                130                 135                 140
```

```
Asp Arg Ser His His Leu Asn Ile Asn Asn Asn Trp Phe Asn Asn Val
145                 150                 155                 160

Thr Ile Leu Tyr Ser Arg Ser Ser Thr Ala Thr Trp Gln Lys Ser Ala
                165                 170                 175

Ala Tyr Val Tyr Gln Gly Val Ser Asn Phe Thr Tyr Tyr Lys Leu Asn
            180                 185                 190

Asn Thr Asn Gly Leu Lys Ser Tyr Glu
                195                 200
```

(2) INFORMATION FOR SEQ ID NO:4:

(i) SEQUENCE CHARACTERISTICS:
        (A) LENGTH: 51 amino acids
        (B) TYPE: amino acid
        (D) TOPOLOGY: unknown (ii) MOLECULE TYPE: protein (xi) SEQUENCE DESCRIPTION: SEQ ID NO:4:

```
Ser Cys Tyr Asn Asp Thr Val Ser Glu Ser Ser Phe Tyr Ser Tyr Gly
1               5                   10                  15

Glu Ile Ser Phe Gly Val Thr Asp Gly Pro Arg Tyr Cys Tyr Ala Leu
                20                  25                  30

Tyr Asn Gly Thr Ala Leu Lys Tyr Leu Gly Thr Leu Pro Pro Ser Val
            35                  40                  45

Lys Glu Ile
    50
```

(2) INFORMATION FOR SEQ ID NO:5:

(i) SEQUENCE CHARACTERISTICS:
        (A) LENGTH: 21 amino acids
        (B) TYPE: amino acid
        (D) TOPOLOGY: unknown (ii) MOLECULE TYPE: protein (xi) SEQUENCE DESCRIPTION: SEQ ID NO:5:

```
Ser Phe Asn Leu Thr Thr Gly Asp Ser Gly Ala Phe Trp Thr Ile Ala
1               5                   10                  15

Tyr Thr Ser Tyr Thr
                20
```

(2) INFORMATION FOR SEQ ID NO:6:

(i) SEQUENCE CHARACTERISTICS:
        (A) LENGTH: 51 amino acids
        (B) TYPE: amino acid
        (D) TOPOLOGY: unknown (ii) MOLECULE TYPE: protein (xi) SEQUENCE DESCRIPTION: SEQ ID NO:6:

```
Pro Ile Ala Ser Thr Leu Ser Asn Ile Thr Leu Pro Met Gln Asp Asn
1               5                   10                  15

Asn Thr Asp Val Tyr Cys Ile Arg Ser Asn Gln Phe Ser Val Tyr Val
                20                  25                  30

His Ser Thr Cys Lys Ser Ser Leu Trp Asp Asp Val Phe Asn Ser Asp
            35                  40                  45

Cys Thr Asp
    50
```

(2) INFORMATION FOR SEQ ID NO:7:

(i) SEQUENCE CHARACTERISTICS:
        (A) LENGTH: 51 amino acids
        (B) TYPE: amino acid
        (D) TOPOLOGY: unknown (ii) MOLECULE TYPE: protein (xi) SEQUENCE DESCRIPTION: SEQ ID NO:7:

```
Thr Asn Glu Gln Val Val Arg Ser Leu Tyr Val Ile Tyr Glu Gly
1               5                  10                  15

Asp Asn Ile Val Gly Val Pro Ser Asp Asn Ser Gly Leu His Asp Leu
            20                  25                  30

Ser Val Leu His Leu Asp Ser Cys Thr Asp Tyr Asn Ile Tyr Gly Arg
        35                  40                  45

Thr Gly Val
    50
```

(2) INFORMATION FOR SEQ ID NO:8:

(i) SEQUENCE CHARACTERISTICS:
        (A) LENGTH: 81 amino acids
        (B) TYPE: amino acid
        (D) TOPOLOGY: unknown (ii) MOLECULE TYPE: protein (xi) SEQUENCE DESCRIPTION: SEQ ID NO:8:

```
Trp Thr Thr Thr Pro Asn Phe Tyr Tyr Tyr Ser Ile Tyr Asn Tyr Thr
1               5                  10                  15

Asn Glu Arg Thr Arg Gly Thr Ala Ile Asp Ser Asn Asp Val Asp Cys
            20                  25                  30

Glu Pro Ile Ile Thr Tyr Ser Asn Ile Gly Val Cys Lys Asn Gly Ala
        35                  40                  45

Leu Val Phe Ile Asn Val Thr His Ser Asp Gly Asp Val Gln Pro Ile
    50                  55                  60

Ser Thr Gly Asn Val Thr Ile Pro Thr Asn Phe Thr Ile Ser Val Gln
65                  70                  75                  80

Val
```

(2) INFORMATION FOR SEQ ID NO:9:

(i) SEQUENCE CHARACTERISTICS:
        (A) LENGTH: 126 amino acids
        (B) TYPE: amino acid
        (D) TOPOLOGY: unknown (ii) MOLECULE TYPE: protein (xi) SEQUENCE DESCRIPTION: SEQ ID NO:9:

```
Glu Asn Met Glu Ile Asp Ser Met Leu Phe Val Ser Glu Asn Ala Leu
1               5                  10                  15

Lys Leu Ala Ser Val Glu Ala Phe Asn Ser Thr Glu Thr Leu Asp Pro
            20                  25                  30

Ile Tyr Lys Glu Trp Pro Asn Ile Gly Gly Ser Trp Leu Gly Gly Leu
        35                  40                  45

Lys Asp Ile Leu Pro Ser His Asn Ser Lys Arg Lys Tyr Arg Ser Ala
    50                  55                  60

Ile Glu Asp Leu Leu Phe Asp Lys Val Val Thr Ser Gly Leu Gly Thr
65                  70                  75                  80
```

```
Val Asp Glu Asp Tyr Lys Arg Cys Thr Gly Tyr Asp Ile Ala Asp
            85                  90                  95

Leu Val Cys Ala Gln Tyr Tyr Asn Gly Ile Met Val Leu Pro Gly Val
            100                 105                 110

Ala Asn Asp Asp Lys Met Ala Met Tyr Thr Ala Ser Leu Ala
            115                 120                 125

(2) INFORMATION FOR SEQ ID NO:10:

(i) SEQUENCE CHARACTERISTICS:
        (A) LENGTH: 76 amino acids
        (B) TYPE: amino acid
        (D) TOPOLOGY: unknown (ii) MOLECULE TYPE: protein (xi) SEQUENCE DESCRIPTION: SEQ ID NO:10:

Gln Val Asp Arg Leu Ile Thr Gly Arg Leu Thr Ala Leu Asn Ala Phe
1               5                   10                  15

Val Ser Gln Thr Leu Thr Arg Gln Ala Glu Val Arg Ala Ser Arg Gln
            20                  25                  30

Leu Ala Lys Asp Lys Val Asn Glu Cys Val Arg Ser Gln Ser Gln Arg
            35                  40                  45

Phe Gly Phe Cys Gly Asn Gly Thr His Leu Phe Ser Leu Ala Asn Ala
50                  55                  60

Ala Pro Asn Gly Met Ile Phe Phe His Thr Val Leu
65                  70                  75

(2) INFORMATION FOR SEQ ID NO:11:

(i) SEQUENCE CHARACTERISTICS:
        (A) LENGTH: 203 amino acids
        (B) TYPE: amino acid
        (D) TOPOLOGY: unknown (ii) MOLECULE TYPE: protein (xi) SEQUENCE DESCRIPTION: SEQ ID NO:11:

Leu Val Val Lys Asp Val Gln Leu Thr Leu Phe Arg Asn Leu Asp Asp
1               5                   10                  15

Lys Phe Tyr Leu Thr Pro Arg Thr Met Tyr Gln Pro Arg Val Ala Thr
            20                  25                  30

Ser Ser Asp Phe Val Gln Ile Glu Gly Cys Asp Val Leu Phe Val Asn
            35                  40                  45

Ala Thr Val Ile Asp Leu Pro Ser Ile Ile Pro Asp Tyr Ile Asp Ile
            50                  55                  60

Asn Gln Thr Val Gln Asp Ile Leu Glu Asn Phe Arg Pro Asn Trp Thr
65                  70                  75                  80

Val Pro Glu Leu Pro Leu Asp Ile Phe Asn Ala Thr Tyr Leu Asn Leu
                85                  90                  95

Thr Gly Glu Ile Asn Asp Leu Glu Phe Arg Ser Glu Lys Leu His Asn
            100                 105                 110

Thr Thr Val Glu Leu Ala Ile Leu Ile Asp Asn Ile Asn Asn Thr Leu
            115                 120                 125

Val Asn Leu Glu Trp Leu Asn Arg Ile Glu Thr Tyr Val Lys Trp Pro
            130                 135                 140

Trp Tyr Val Trp Leu Leu Ile Gly Leu Val Val Ile Phe Cys Ile Pro
145                 150                 155                 160
```

```
Ile Leu Leu Phe Cys Cys Cys Ser Thr Gly Cys Cys Gly Cys Ile Gly
            165                 170                 175

Cys Leu Gly Ser Cys Cys His Ser Ile Cys Ser Arg Arg Arg Phe Glu
            180                 185                 190

Ser Tyr Glu Pro Ile Glu Lys Val His Val His
            195                 200
```

(2) INFORMATION FOR SEQ ID NO:12:

(i) SEQUENCE CHARACTERISTICS:
        (A) LENGTH: 8 amino acids
        (B) TYPE: amino acid
        (D) TOPOLOGY: unknown (ii) MOLECULE TYPE: protein (xi) SEQUENCE DESCRIPTION: SEQ ID NO:12:

```
Asp Phe Leu Phe His Thr Phe Lys
1               5
```

(2) INFORMATION FOR SEQ ID NO:13:

(i) SEQUENCE CHARACTERISTICS:
        (A) LENGTH: 19 amino acids
        (B) TYPE: amino acid
        (D) TOPOLOGY: unknown (ii) MOLECULE TYPE: protein (xi) SEQUENCE DESCRIPTION: SEQ ID NO:13:

```
Trp Tyr Asn Cys Ser Arg Ser Ala Thr Thr Thr Ala Tyr Lys Asp Phe
1               5                   10                  15

Ser Asn Ile
```

(2) INFORMATION FOR SEQ ID NO:14:

(i) SEQUENCE CHARACTERISTICS:
        (A) LENGTH: 5 amino acids
        (B) TYPE: amino acid
        (D) TOPOLOGY: unknown (ii) MOLECULE TYPE: protein (xi) SEQUENCE DESCRIPTION: SEQ ID NO:14:

```
Tyr Val Thr Ala Tyr
1               5
```

(2) INFORMATION FOR SEQ ID NO:15:

(i) SEQUENCE CHARACTERISTICS:
        (A) LENGTH: 34 amino acids
        (B) TYPE: amino acid
        (D) TOPOLOGY: unknown (ii) MOLECULE TYPE: protein (xi) SEQUENCE DESCRIPTION: SEQ ID NO:15:

```
Asn Asn Thr Asn Gly Leu Lys Ser Tyr Glu Leu Cys Glu Asp Tyr Glu
1               5                   10                  15

Cys Cys Thr Gly Tyr Ala Thr Asn Val Phe Ala Pro Thr Val Gly Gly
            20                  25                  30

Tyr Ile
```

(2) INFORMATION FOR SEQ ID NO:16:

```
        (i) SEQUENCE CHARACTERISTICS:
             (A) LENGTH: 7 amino acids
             (B) TYPE: amino acid
             (D) TOPOLOGY: unknown (ii) MOLECULE TYPE: protein (xi) SEQUENCE DESCRIPTION: SEQ ID NO:16:

Ser Leu Asn Asn Thr Val Asp
1               5

(2) INFORMATION FOR SEQ ID NO:17:

(i) SEQUENCE CHARACTERISTICS:
             (A) LENGTH: 34 amino acids
             (B) TYPE: amino acid
             (D) TOPOLOGY: unknown (ii) MOLECULE TYPE: protein (xi) SEQUENCE DESCRIPTION: SEQ ID NO:17:

Gly Val Thr Asp Gly Pro Arg Tyr Cys Tyr Ala Leu Tyr Asn Gly Thr
1               5                   10                  15

Ala Leu Lys Tyr Leu Gly Thr Leu Pro Pro Ser Val Lys Glu Ile Ala
            20                  25                  30

Ile Ser (2) INFORMATION FOR SEQ ID NO:18:

(i) SEQUENCE CHARACTERISTICS:
             (A) LENGTH: 27 amino acids
             (B) TYPE: amino acid
             (D) TOPOLOGY: unknown (ii) MOLECULE TYPE: protein (xi) SEQUENCE DESCRIPTION: SEQ ID NO:18:

Ser Tyr Thr Asp Ala Leu Val Gln Val Glu Asn Thr Ala Ile Lys Lys
1               5                   10                  15

Val Thr Tyr Cys Asn Ser His Ile Asn Asn Ile
            20                  25

(2) INFORMATION FOR SEQ ID NO:19:

(i) SEQUENCE CHARACTERISTICS:
             (A) LENGTH: 15 amino acids
             (B) TYPE: amino acid
             (D) TOPOLOGY: unknown (ii) MOLECULE TYPE: protein (xi) SEQUENCE DESCRIPTION: SEQ ID NO:19:

Ile Ser Val Gln Val Glu Tyr Ile Gln Val Tyr Thr Thr Pro Val
1               5                   10                  15

(2) INFORMATION FOR SEQ ID NO:20:

(i) SEQUENCE CHARACTERISTICS:
             (A) LENGTH: 37 amino acids
             (B) TYPE: amino acid
             (D) TOPOLOGY: unknown (ii) MOLECULE TYPE: protein (xi) SEQUENCE DESCRIPTION: SEQ ID NO:20:

Lys Leu Ala Ser Val Glu Ala Phe Asn Ser Thr Glu Thr Leu Asp Pro
1               5                   10                  15
```

```
Ile Tyr Lys Glu Trp Pro Asn Ile Gly Gly Ser Trp Leu Gly Gly Leu
        20                  25                  30

Lys Asp Ile Leu Pro
        35
```

(2) INFORMATION FOR SEQ ID NO:21:

(i) SEQUENCE CHARACTERISTICS:
        (A) LENGTH: 16 amino acids
        (B) TYPE: amino acid
        (D) TOPOLOGY: unknown (ii) MOLECULE TYPE: protein (xi) SEQUENCE DESCRIPTION: SEQ ID NO:21:

```
Leu Gly Thr Val Asp Glu Asp Tyr Lys Arg Cys Thr Gly Gly Tyr Asp
1               5                   10                  15
```

(2) INFORMATION FOR SEQ ID NO:22:

(i) SEQUENCE CHARACTERISTICS:
        (A) LENGTH: 78 amino acids
        (B) TYPE: amino acid
        (D) TOPOLOGY: unknown (ii) MOLECULE TYPE: protein (xi) SEQUENCE DESCRIPTION: SEQ ID NO:22:

```
Ala Asn Ala Phe Asn Gln Ala Ile Gly Asn Ile Thr Gln Ala Phe Gly
1               5                   10                  15

Lys Val Asn Asp Ala Ile His Gln Thr Ser Gln Gly Leu Ala Thr Val
        20                  25                  30

Ala Lys Ala Leu Ala Lys Val Gln Asp Val Val Asn Thr Gln Gly Gln
            35                  40                  45

Ala Leu Ser His Leu Thr Val Gln Leu Gln Asn Asn Phe Gln Ala Ile
        50                  55                  60

Ser Ser Ser Ile Ser Asp Ile Tyr Asn Arg Leu Asp Glu Leu
65                  70                  75
```

(2) INFORMATION FOR SEQ ID NO:23:

(i) SEQUENCE CHARACTERISTICS:
        (A) LENGTH: 26 amino acids
        (B) TYPE: amino acid
        (D) TOPOLOGY: unknown (ii) MOLECULE TYPE: protein (xi) SEQUENCE DESCRIPTION: SEQ ID NO:23:

```
Leu Ala Ile Leu Ile Asp Asn Ile Asn Asn Thr Leu Val Asn Leu Glu
1               5                   10                  15

Trp Leu Asn Arg Ile Glu Thr Tyr Val Lys
        20                  25
```

(2) INFORMATION FOR SEQ ID NO:24:

(i) SEQUENCE CHARACTERISTICS:
        (A) LENGTH: 372 base pairs
        (B) TYPE: nucleic acid
        (C) STRANDEDNESS: double
        (D) TOPOLOGY: unknown (ii) MOLECULE TYPE: DNA (genomic)

(ix) FEATURE:

```
        (A) NAME/KEY: CDS
        (B) LOCATION: 1..372

(xi) SEQUENCE DESCRIPTION: SEQ ID NO:24:

CAA GGG CAA GCT TTA AGC CAC CTA ACA GTA CAA TTG CAA AAT AAT TTC        48
Gln Gly Gln Ala Leu Ser His Leu Thr Val Gln Leu Gln Asn Asn Phe
 1               5                  10                  15

CAA GCC ATT AGT AGT TCC ATT AGT GAC ATT TAT AAC AGG CTT GAT GAA        96
Gln Ala Ile Ser Ser Ser Ile Ser Asp Ile Tyr Asn Arg Leu Asp Glu
             20                  25                  30

TTG AGT GCT GAT GCA CAA GTT GAC AGG CTG ATT ACA GGA AGA CTT ACA       144
Leu Ser Ala Asp Ala Gln Val Asp Arg Leu Ile Thr Gly Arg Leu Thr
         35                  40                  45

GCA CTT AAT GCA TTT GTG TCT CAG ACT TTA ACC AGA CAA GCA GAG GTT       192
Ala Leu Asn Ala Phe Val Ser Gln Thr Leu Thr Arg Gln Ala Glu Val
     50                  55                  60

AGG GCT AGC AGA CAG CTT GCT AAA GAC AAG GTA AAT GAA TGC GTT AGG       240
Arg Ala Ser Arg Gln Leu Ala Lys Asp Lys Val Asn Glu Cys Val Arg
 65                  70                  75                  80

TCT CAA TCT CAG AGA TTT GGA TTC TGT GGT AAT GGT ACA CAT TTA TTT       288
Ser Gln Ser Gln Arg Phe Gly Phe Cys Gly Asn Gly Thr His Leu Phe
                 85                  90                  95

TCA CTT GCA AAT GCA GCA CCA AAT GGC ATG ATC TTC TTT CAC ACA GTG       336
Ser Leu Ala Asn Ala Ala Pro Asn Gly Met Ile Phe Phe His Thr Val
             100                 105                 110

CTA TTA CCA ACA GCT TAT GAA ACC GTG ACG GCC TGG                       372
Leu Leu Pro Thr Ala Tyr Glu Thr Val Thr Ala Trp
         115                 120

(2) INFORMATION FOR SEQ ID NO:25:

(i) SEQUENCE CHARACTERISTICS:
        (A) LENGTH: 124 amino acids
        (B) TYPE: amino acid
        (D) TOPOLOGY: linear (ii) MOLECULE TYPE: protein (xi) SEQUENCE DESCRIPTION: SEQ ID NO:25:

Gln Gly Gln Ala Leu Ser His Leu Thr Val Gln Leu Gln Asn Asn Phe
 1               5                  10                  15

Gln Ala Ile Ser Ser Ser Ile Ser Asp Ile Tyr Asn Arg Leu Asp Glu
             20                  25                  30

Leu Ser Ala Asp Ala Gln Val Asp Arg Leu Ile Thr Gly Arg Leu Thr
         35                  40                  45

Ala Leu Asn Ala Phe Val Ser Gln Thr Leu Thr Arg Gln Ala Glu Val
     50                  55                  60

Arg Ala Ser Arg Gln Leu Ala Lys Asp Lys Val Asn Glu Cys Val Arg
 65                  70                  75                  80

Ser Gln Ser Gln Arg Phe Gly Phe Cys Gly Asn Gly Thr His Leu Phe
                 85                  90                  95

Ser Leu Ala Asn Ala Ala Pro Asn Gly Met Ile Phe Phe His Thr Val
             100                 105                 110

Leu Leu Pro Thr Ala Tyr Glu Thr Val Thr Ala Trp
         115                 120

(2) INFORMATION FOR SEQ ID NO:26:

(i) SEQUENCE CHARACTERISTICS:
        (A) LENGTH: 180 base pairs
        (B) TYPE: nucleic acid
```

(C) STRANDEDNESS: double
        (D) TOPOLOGY: unknown (ii) MOLECULE TYPE: DNA (genomic)

(ix) FEATURE:
        (A) NAME/KEY: CDS
        (B) LOCATION: 1..180

(xi) SEQUENCE DESCRIPTION: SEQ ID NO:26:

```
CTT GGT ATG AAG CGT AGT GGT TAT GGT CAA CCC ATA GCC TCA ACA TTA      48
Leu Gly Met Lys Arg Ser Gly Tyr Gly Gln Pro Ile Ala Ser Thr Leu
 1               5                  10                  15

AGT AAC ATC ACA CTA CCA ATG CAG GAT AAT AAC ACC GAT GTG TAC TGC      96
Ser Asn Ile Thr Leu Pro Met Gln Asp Asn Asn Thr Asp Val Tyr Cys
             20                  25                  30

ATT CGT TCT AAC CAA TTT TCA GTT TAC GTT CAT TCC ACT TGT AAA AGT     144
Ile Arg Ser Asn Gln Phe Ser Val Tyr Val His Ser Thr Cys Lys Ser
         35                  40                  45

TCT TTA TGG GAC GAT GTG TTT AAT TCC GAC TGC ACA                     180
Ser Leu Trp Asp Asp Val Phe Asn Ser Asp Cys Thr
     50                  55                  60
```

(2) INFORMATION FOR SEQ ID NO:27:

(i) SEQUENCE CHARACTERISTICS:
        (A) LENGTH: 60 amino acids
        (B) TYPE: amino acid
        (D) TOPOLOGY: linear (ii) MOLECULE TYPE: protein (xi) SEQUENCE DESCRIPTION: SEQ ID NO:27:

```
Leu Gly Met Lys Arg Ser Gly Tyr Gly Gln Pro Ile Ala Ser Thr Leu
 1               5                  10                  15

Ser Asn Ile Thr Leu Pro Met Gln Asp Asn Asn Thr Asp Val Tyr Cys
             20                  25                  30

Ile Arg Ser Asn Gln Phe Ser Val Tyr Val His Ser Thr Cys Lys Ser
         35                  40                  45

Ser Leu Trp Asp Asp Val Phe Asn Ser Asp Cys Thr
     50                  55                  60
```

(2) INFORMATION FOR SEQ ID NO:28:

(i) SEQUENCE CHARACTERISTICS:
        (A) LENGTH: 141 base pairs
        (B) TYPE: nucleic acid
        (C) STRANDEDNESS: double
        (D) TOPOLOGY: unknown (ii) MOLECULE TYPE: DNA (genomic)

(ix) FEATURE:
        (A) NAME/KEY: CDS
        (B) LOCATION: 1..141

(xi) SEQUENCE DESCRIPTION: SEQ ID NO:28:

```
GTC ATT AGA TTC AAC CTT AAT TTT ACC ACA GAT GTA CAA TCT GGT ATG      48
Val Ile Arg Phe Asn Leu Asn Phe Thr Thr Asp Val Gln Ser Gly Met
 1               5                  10                  15

GGT GCT ACA GTA TTT TCA CTG AAT ACA ACA GGT GGT GTC ATT CTT GAG      96
Gly Ala Thr Val Phe Ser Leu Asn Thr Thr Gly Gly Val Ile Leu Glu
             20                  25                  30

ATT TCT TGT TAT AAT GAT ACA GTG AGT GAG TCA AGT TTC TAC AGT         141
Ile Ser Cys Tyr Asn Asp Thr Val Ser Glu Ser Ser Phe Tyr Ser
         35                  40                  45
```

(2) INFORMATION FOR SEQ ID NO:29:

(i) SEQUENCE CHARACTERISTICS:
        (A) LENGTH: 47 amino acids
        (B) TYPE: amino acid
        (D) TOPOLOGY: linear (ii) MOLECULE TYPE: protein (xi) SEQUENCE DESCRIPTION: SEQ ID NO:29:

```
Val Ile Arg Phe Asn Leu Asn Phe Thr Thr Asp Val Gln Ser Gly Met
 1               5                  10                  15

Gly Ala Thr Val Phe Ser Leu Asn Thr Thr Gly Gly Val Ile Leu Glu
            20                  25                  30

Ile Ser Cys Tyr Asn Asp Thr Val Ser Glu Ser Ser Phe Tyr Ser
        35                  40                  45
```

(2) INFORMATION FOR SEQ ID NO:30:

(i) SEQUENCE CHARACTERISTICS:
        (A) LENGTH: 51 base pairs
        (B) TYPE: nucleic acid
        (C) STRANDEDNESS: double
        (D) TOPOLOGY: unknown (ii) MOLECULE TYPE: DNA (genomic)

(ix) FEATURE:
        (A) NAME/KEY: CDS
        (B) LOCATION: 1..51

(xi) SEQUENCE DESCRIPTION: SEQ ID NO:30:

```
TGT ATA ACT AAA AAT AAA ATC ATT GAC TAT AAC ACG TTT ACC AGC GCA      48
Cys Ile Thr Lys Asn Lys Ile Ile Asp Tyr Asn Thr Phe Thr Ser Ala
 1               5                  10                  15

CAG                                                                  51
Gln
```

(2) INFORMATION FOR SEQ ID NO:31:

(i) SEQUENCE CHARACTERISTICS:
        (A) LENGTH: 17 amino acids
        (B) TYPE: amino acid
        (D) TOPOLOGY: linear (ii) MOLECULE TYPE: protein (xi) SEQUENCE DESCRIPTION: SEQ ID NO:31:

```
Cys Ile Thr Lys Asn Lys Ile Ile Asp Tyr Asn Thr Phe Thr Ser Ala
 1               5                  10                  15

Gln
```

(2) INFORMATION FOR SEQ ID NO:32:

(i) SEQUENCE CHARACTERISTICS:
        (A) LENGTH: 42 base pairs
        (B) TYPE: nucleic acid
        (C) STRANDEDNESS: double
        (D) TOPOLOGY: unknown (ii) MOLECULE TYPE: DNA (genomic)

(ix) FEATURE:
        (A) NAME/KEY: CDS
        (B) LOCATION: 1..42

(xi) SEQUENCE DESCRIPTION: SEQ ID NO:32:

```
TCT TGT TAT AAT GAT ACA GTG AGT GAG TCA AGT TTC TAC AGT              42
Ser Cys Tyr Asn Asp Thr Val Ser Glu Ser Ser Phe Tyr Ser
 1               5                  10
```

(2) INFORMATION FOR SEQ ID NO:33:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO:33:

```
Ser Cys Tyr Asn Asp Thr Val Ser Glu Ser Ser Phe Tyr Ser
 1               5                  10
```

(2) INFORMATION FOR SEQ ID NO:34:

(i) SEQUENCE CHARACTERISTICS:
        (A) LENGTH: 51 base pairs
        (B) TYPE: nucleic acid
        (C) STRANDEDNESS: double
        (D) TOPOLOGY: unknown (ii) MOLECULE TYPE: DNA (genomic)

(ix) FEATURE:
        (A) NAME/KEY: CDS
        (B) LOCATION: 1..51

(xi) SEQUENCE DESCRIPTION: SEQ ID NO:34:

```
ATT GGG TGT TTA GGA AGC TGT TGT CAT TCC ATA TGT AGT AGA AGG CGA      48
Ile Gly Cys Leu Gly Ser Cys Cys His Ser Ile Cys Ser Arg Arg Arg
 1               5                  10                  15

TTT                                                                  51
Phe
```

(2) INFORMATION FOR SEQ ID NO:35:

(i) SEQUENCE CHARACTERISTICS:
        (A) LENGTH: 17 amino acids
        (B) TYPE: amino acid
        (D) TOPOLOGY: linear (ii) MOLECULE TYPE: protein (xi) SEQUENCE DESCRIPTION: SEQ ID NO:35:

```
Ile Gly Cys Leu Gly Ser Cys Cys His Ser Ile Cys Ser Arg Arg Arg
 1               5                  10                  15

Phe
```

(2) INFORMATION FOR SEQ ID NO:36:

(i) SEQUENCE CHARACTERISTICS:
        (A) LENGTH: 42 base pairs
        (B) TYPE: nucleic acid
        (C) STRANDEDNESS: double
        (D) TOPOLOGY: unknown (ii) MOLECULE TYPE: DNA (genomic)

(ix) FEATURE:
        (A) NAME/KEY: CDS
        (B) LOCATION: 1..42

(xi) SEQUENCE DESCRIPTION: SEQ ID NO:36:

```
TGC ATA CCC ATA TTG CTA TTT TGT TGT TGT AGC ACT GGT TGT              42
```

```
Cys Ile Pro Ile Leu Leu Phe Cys Cys Cys Ser Thr Gly Cys
 1               5                  10
```

(2) INFORMATION FOR SEQ ID NO:37:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO:37:

```
Cys Ile Pro Ile Leu Leu Phe Cys Cys Cys Ser Thr Gly Cys
 1               5                  10
```

(2) INFORMATION FOR SEQ ID NO:38:

(i) SEQUENCE CHARACTERISTICS:
        (A) LENGTH: 195 base pairs
        (B) TYPE: nucleic acid
        (C) STRANDEDNESS: double
        (D) TOPOLOGY: unknown (ii) MOLECULE TYPE: DNA (genomic)

(ix) FEATURE:
        (A) NAME/KEY: CDS
        (B) LOCATION: 1..195

(xi) SEQUENCE DESCRIPTION: SEQ ID NO:38:

```
TAC TTA AAC CTG ACT GGT GAA ATT AAT GAC TTA GAA TTT AGG TCA GAA         48
Tyr Leu Asn Leu Thr Gly Glu Ile Asn Asp Leu Glu Phe Arg Ser Glu
 1               5                  10                  15

AAG TTA CAT AAC ACC ACA GTA GAA CTT GCT ATT CTC ATT GAT AAT ATT         96
Lys Leu His Asn Thr Thr Val Glu Leu Ala Ile Leu Ile Asp Asn Ile
                20                  25                  30

AAT AAC ACA TTA GTC AAT CTT GAA TGG CTC AAT AGA ATT GAA ACT TAT        144
Asn Asn Thr Leu Val Asn Leu Glu Trp Leu Asn Arg Ile Glu Thr Tyr
            35                  40                  45

GTA AAA TGG CCT TGG TAT GTG TGG CTA CTA ATT GGA TTA GTA GTA ATA        192
Val Lys Trp Pro Trp Tyr Val Trp Leu Leu Ile Gly Leu Val Val Ile
        50                  55                  60

TTC                                                                    195
Phe
65
```

(2) INFORMATION FOR SEQ ID NO:39:

(i) SEQUENCE CHARACTERISTICS:
        (A) LENGTH: 65 amino acids
        (B) TYPE: amino acid
        (D) TOPOLOGY: linear (ii) MOLECULE TYPE: protein (xi) SEQUENCE DESCRIPTION: SEQ ID NO:39:

```
Tyr Leu Asn Leu Thr Gly Glu Ile Asn Asp Leu Glu Phe Arg Ser Glu
 1               5                  10                  15

Lys Leu His Asn Thr Thr Val Glu Leu Ala Ile Leu Ile Asp Asn Ile
                20                  25                  30

Asn Asn Thr Leu Val Asn Leu Glu Trp Leu Asn Arg Ile Glu Thr Tyr
            35                  40                  45

Val Lys Trp Pro Trp Tyr Val Trp Leu Leu Ile Gly Leu Val Val Ile
        50                  55                  60
```

Phe
65

(2) INFORMATION FOR SEQ ID NO:40:

(i) SEQUENCE CHARACTERISTICS:
        (A) LENGTH: 765 base pairs
        (B) TYPE: nucleic acid
        (C) STRANDEDNESS: double
        (D) TOPOLOGY: unknown (ii) MOLECULE TYPE: DNA (genomic)

(ix) FEATURE:
        (A) NAME/KEY: CDS
        (B) LOCATION: 1..765

(xi) SEQUENCE DESCRIPTION: SEQ ID NO:40:

```
GAT GGA CCG CGT TAC TGT TAC GCA CTC TAT AAT GGC ACG GCT CTT AAG        48
Asp Gly Pro Arg Tyr Cys Tyr Ala Leu Tyr Asn Gly Thr Ala Leu Lys
 1               5                  10                  15

TAT TTA GGA ACA TTA CCA CCT AGT GTC AAG GAA ATT GCT ATT AGT AAG        96
Tyr Leu Gly Thr Leu Pro Pro Ser Val Lys Glu Ile Ala Ile Ser Lys
                20                  25                  30

TGG GGC CAT TTT TAT ATT AAT GGT TAC AAT TTC TTT AGC ACT TTT CCT       144
Trp Gly His Phe Tyr Ile Asn Gly Tyr Asn Phe Phe Ser Thr Phe Pro
            35                  40                  45

ATT GAT TGT ATA TCT TTT AAT TTA ACC ACT GGT GAT AGT GGA GCA TTT       192
Ile Asp Cys Ile Ser Phe Asn Leu Thr Thr Gly Asp Ser Gly Ala Phe
        50                  55                  60

TGG ACA ATT GCT TAC ACA TCG TAC ACT GAC GCA TTA GTA CAA GTT GAA       240
Trp Thr Ile Ala Tyr Thr Ser Tyr Thr Asp Ala Leu Val Gln Val Glu
65                  70                  75                  80

AAC ACA GCT ATT AAA AAG GTG ACG TAT TGT AAC AGT CAC ATT AAT AAC       288
Asn Thr Ala Ile Lys Lys Val Thr Tyr Cys Asn Ser His Ile Asn Asn
                85                  90                  95

ATT AAA TGT TCT CAA CTT ACT GCT AAT TTG CAA AAT GGA TTT TAT CCT       336
Ile Lys Cys Ser Gln Leu Thr Ala Asn Leu Gln Asn Gly Phe Tyr Pro
            100                 105                 110

GTT GCT TCA AGT GAA GTT GGT CTT GTC AAT AAG AGT GTT GTG TTA CTA       384
Val Ala Ser Ser Glu Val Gly Leu Val Asn Lys Ser Val Val Leu Leu
        115                 120                 125

CCT AGT TTC TAT TCA CAT ACC AGT GTT AAT ATA ACT ATT GAT CTT GGT       432
Pro Ser Phe Tyr Ser His Thr Ser Val Asn Ile Thr Ile Asp Leu Gly
130                 135                 140

ATG AAG CGT AGT GGT TAT GGT CAA CCC ATA GCC TCA ACA TTA AGT AAC       480
Met Lys Arg Ser Gly Tyr Gly Gln Pro Ile Ala Ser Thr Leu Ser Asn
145                 150                 155                 160

ATC ACA CTA CCA ATG CAG GAT AAT AAC ACC GAT GTG TAC TGC ATT CGT       528
Ile Thr Leu Pro Met Gln Asp Asn Asn Thr Asp Val Tyr Cys Ile Arg
                165                 170                 175

TCT AAC CAA TTT TCA GTT TAC GTT CAT TCC ACT TGT AAA AGT TCT TTA       576
Ser Asn Gln Phe Ser Val Tyr Val His Ser Thr Cys Lys Ser Ser Leu
            180                 185                 190

TGG GAC GAT GTG TTT AAT TCC GAC TGC ACA GAT GTT TTA TAT GCT ACA       624
Trp Asp Asp Val Phe Asn Ser Asp Cys Thr Asp Val Leu Tyr Ala Thr
        195                 200                 205

GCT GTT ATA AAA ACT GGT ACT TGT CCT TTC TCG TTT GAT AAA TTG AAC       672
Ala Val Ile Lys Thr Gly Thr Cys Pro Phe Ser Phe Asp Lys Leu Asn
210                 215                 220

AAT TAC TTA ACT TTT AAC AAG TTC TGT TTG TCA TTG AAT CCT GTT GGT       720
Asn Tyr Leu Thr Phe Asn Lys Phe Cys Leu Ser Leu Asn Pro Val Gly
225                 230                 235                 240
```

```
GCC AAC TGC AAG TTT GAT GTT GCC GCT CGT ACA AGA ACC AAT GAG                    765
Ala Asn Cys Lys Phe Asp Val Ala Ala Arg Thr Arg Thr Asn Glu
            245                 250                 255
```

(2) INFORMATION FOR SEQ ID NO:41:

(i) SEQUENCE CHARACTERISTICS:
        (A) LENGTH: 255 amino acids
        (B) TYPE: amino acid
        (D) TOPOLOGY: linear (ii) MOLECULE TYPE: protein (xi) SEQUENCE DESCRIPTION: SEQ ID NO:41:

```
Asp Gly Pro Arg Tyr Cys Tyr Ala Leu Tyr Asn Gly Thr Ala Leu Lys
 1               5                  10                  15

Tyr Leu Gly Thr Leu Pro Pro Ser Val Lys Glu Ile Ala Ile Ser Lys
             20                  25                  30

Trp Gly His Phe Tyr Ile Asn Gly Tyr Asn Phe Phe Ser Thr Phe Pro
             35                  40                  45

Ile Asp Cys Ile Ser Phe Asn Leu Thr Thr Gly Asp Ser Gly Ala Phe
 50                  55                  60

Trp Thr Ile Ala Tyr Thr Ser Tyr Thr Asp Ala Leu Val Gln Val Glu
 65                  70                  75                  80

Asn Thr Ala Ile Lys Lys Val Thr Tyr Cys Asn Ser His Ile Asn Asn
                 85                  90                  95

Ile Lys Cys Ser Gln Leu Thr Ala Asn Leu Gln Asn Gly Phe Tyr Pro
                100                 105                 110

Val Ala Ser Ser Glu Val Gly Leu Val Asn Lys Ser Val Val Leu Leu
             115                 120                 125

Pro Ser Phe Tyr Ser His Thr Ser Val Asn Ile Thr Ile Asp Leu Gly
130                 135                 140

Met Lys Arg Ser Gly Tyr Gly Gln Pro Ile Ala Ser Thr Leu Ser Asn
145                 150                 155                 160

Ile Thr Leu Pro Met Gln Asp Asn Asn Thr Asp Val Tyr Cys Ile Arg
                165                 170                 175

Ser Asn Gln Phe Ser Val Tyr Val His Ser Thr Cys Lys Ser Ser Leu
            180                 185                 190

Trp Asp Asp Val Phe Asn Ser Asp Cys Thr Asp Val Leu Tyr Ala Thr
            195                 200                 205

Ala Val Ile Lys Thr Gly Thr Cys Pro Phe Ser Phe Asp Lys Leu Asn
        210                 215                 220

Asn Tyr Leu Thr Phe Asn Lys Phe Cys Leu Ser Leu Asn Pro Val Gly
225                 230                 235                 240

Ala Asn Cys Lys Phe Asp Val Ala Ala Arg Thr Arg Thr Asn Glu
            245                 250                 255
```

(2) INFORMATION FOR SEQ ID NO:42:

(i) SEQUENCE CHARACTERISTICS:
        (A) LENGTH: 1284 base pairs
        (B) TYPE: nucleic acid
        (C) STRANDEDNESS: double
        (D) TOPOLOGY: unknown (ii) MOLECULE TYPE: DNA (genomic)

(ix) FEATURE:
        (A) NAME/KEY: CDS
        (B) LOCATION: 1..1284

(xi) SEQUENCE DESCRIPTION: SEQ ID NO:42:

| | | | | | | | | | | | | | | | | |
|---|---|---|---|---|---|---|---|---|---|---|---|---|---|---|---|---|
| AGG | CCT | CTT | TTA | AAA | CAT | GGT | TTG | TTG | TGT | ATA | ACT | AAA | AAT | AAA | ATC | 48 |
| Arg | Pro | Leu | Leu | Lys | His | Gly | Leu | Leu | Cys | Ile | Thr | Lys | Asn | Lys | Ile | |
| 1 | | | | 5 | | | | | 10 | | | | | 15 | | |
| ATT | GAC | TAT | AAC | ACG | TTT | ACC | AGC | GCA | CAG | TGG | AGT | GCC | ATA | TGT | TTG | 96 |
| Ile | Asp | Tyr | Asn | Thr | Phe | Thr | Ser | Ala | Gln | Trp | Ser | Ala | Ile | Cys | Leu | |
| | | | 20 | | | | | 25 | | | | | 30 | | | |
| GGT | GAT | GAC | AGA | AAA | ATA | CCA | TTC | TCT | GTC | ATA | CCC | ACA | GGT | AAT | GGT | 144 |
| Gly | Asp | Asp | Arg | Lys | Ile | Pro | Phe | Ser | Val | Ile | Pro | Thr | Gly | Asn | Gly | |
| | | 35 | | | | | 40 | | | | | 45 | | | | |
| ACA | AAA | ATA | TTT | GGT | CTT | GAG | TGG | AAT | GAT | GAC | TAT | GTT | ACA | GCC | TAT | 192 |
| Thr | Lys | Ile | Phe | Gly | Leu | Glu | Trp | Asn | Asp | Asp | Tyr | Val | Thr | Ala | Tyr | |
| | 50 | | | | | 55 | | | | | 60 | | | | | |
| ATT | AGT | GAT | CGT | TCT | CAC | CAT | TTG | AAC | ATC | AAT | AAT | AAT | TGG | TTT | AAC | 240 |
| Ile | Ser | Asp | Arg | Ser | His | His | Leu | Asn | Ile | Asn | Asn | Asn | Trp | Phe | Asn | |
| 65 | | | | | 70 | | | | | 75 | | | | | 80 | |
| AAT | GTG | ACA | ATC | CTA | TAC | TCT | CGA | TCA | AGC | ACT | GCT | ACG | TGG | CAG | AAG | 288 |
| Asn | Val | Thr | Ile | Leu | Tyr | Ser | Arg | Ser | Ser | Thr | Ala | Thr | Trp | Gln | Lys | |
| | | | | 85 | | | | | 90 | | | | | 95 | | |
| AGT | GCT | GCA | TAT | GTT | TAT | CAA | GGT | GTT | TCA | AAT | TTT | ACT | TAT | TAC | AAG | 336 |
| Ser | Ala | Ala | Tyr | Val | Tyr | Gln | Gly | Val | Ser | Asn | Phe | Thr | Tyr | Tyr | Lys | |
| | | | 100 | | | | | 105 | | | | | 110 | | | |
| TTA | AAT | AAC | ACC | AAT | GGC | TTG | AAA | AGC | TAT | GAA | TTG | TGT | GAA | GAT | TAT | 384 |
| Leu | Asn | Asn | Thr | Asn | Gly | Leu | Lys | Ser | Tyr | Glu | Leu | Cys | Glu | Asp | Tyr | |
| | | 115 | | | | | 120 | | | | | 125 | | | | |
| GAA | TGC | TGC | ACT | GGC | TAT | GCT | ACC | AAC | GTA | TTT | GCC | CCG | ACA | GTG | GGC | 432 |
| Glu | Cys | Cys | Thr | Gly | Tyr | Ala | Thr | Asn | Val | Phe | Ala | Pro | Thr | Val | Gly | |
| | 130 | | | | | 135 | | | | | 140 | | | | | |
| GGT | TAT | ATA | CCT | GAT | GGC | TTC | AGT | TTT | AAC | AAT | TGG | TTT | ATG | CTT | ACA | 480 |
| Gly | Tyr | Ile | Pro | Asp | Gly | Phe | Ser | Phe | Asn | Asn | Trp | Phe | Met | Leu | Thr | |
| 145 | | | | | 150 | | | | | 155 | | | | | 160 | |
| AAC | AGT | TCC | ACG | TTT | GTT | AGT | GGC | AGA | TTT | GTA | ACA | AAT | CAA | CCA | TTA | 528 |
| Asn | Ser | Ser | Thr | Phe | Val | Ser | Gly | Arg | Phe | Val | Thr | Asn | Gln | Pro | Leu | |
| | | | | 165 | | | | | 170 | | | | | 175 | | |
| TTG | GTT | AAT | TGT | TTG | TGG | CCA | GTG | CCC | AGT | CTT | GGT | GTC | GCA | GCA | CAA | 576 |
| Leu | Val | Asn | Cys | Leu | Trp | Pro | Val | Pro | Ser | Leu | Gly | Val | Ala | Ala | Gln | |
| | | | 180 | | | | | 185 | | | | | 190 | | | |
| GAA | TTT | TGT | TTT | GAA | GGT | GCG | CAG | TTT | AGC | CAA | TGT | AAT | GGT | GTG | TCT | 624 |
| Glu | Phe | Cys | Phe | Glu | Gly | Ala | Gln | Phe | Ser | Gln | Cys | Asn | Gly | Val | Ser | |
| | | 195 | | | | | 200 | | | | | 205 | | | | |
| TTA | AAC | AAT | ACA | GTG | GAT | GTC | ATT | AGA | TTC | AAC | CTT | AAT | TTT | ACC | ACA | 672 |
| Leu | Asn | Asn | Thr | Val | Asp | Val | Ile | Arg | Phe | Asn | Leu | Asn | Phe | Thr | Thr | |
| | 210 | | | | | 215 | | | | | 220 | | | | | |
| GAT | GTA | CAA | TCT | GGT | ATG | GGT | GCT | ACA | GTA | TTT | TCA | CTG | AAT | ACA | ACA | 720 |
| Asp | Val | Gln | Ser | Gly | Met | Gly | Ala | Thr | Val | Phe | Ser | Leu | Asn | Thr | Thr | |
| 225 | | | | | 230 | | | | | 235 | | | | | 240 | |
| GGT | GGT | GTC | ATT | CTT | GAG | ATT | TCT | TGT | TAT | AAT | GAT | ACA | GTG | AGT | GAG | 768 |
| Gly | Gly | Val | Ile | Leu | Glu | Ile | Ser | Cys | Tyr | Asn | Asp | Thr | Val | Ser | Glu | |
| | | | | 245 | | | | | 250 | | | | | 255 | | |
| TCA | AGT | TTC | TAC | AGT | TAT | GGT | GAA | ATT | TCA | TTC | GGC | GTA | ACT | GAT | GGA | 816 |
| Ser | Ser | Phe | Tyr | Ser | Tyr | Gly | Glu | Ile | Ser | Phe | Gly | Val | Thr | Asp | Gly | |
| | | | 260 | | | | | 265 | | | | | 270 | | | |
| CCG | CGT | TAC | TGT | TAC | GCA | CTC | TAT | AAT | GGC | ACG | GCT | CTT | AAG | TAT | TTA | 864 |
| Pro | Arg | Tyr | Cys | Tyr | Ala | Leu | Tyr | Asn | Gly | Thr | Ala | Leu | Lys | Tyr | Leu | |
| | | 275 | | | | | 280 | | | | | 285 | | | | |
| GGA | ACA | TTA | CCA | CCT | AGT | GTC | AAG | GAA | ATT | GCT | ATT | AGT | AAG | TGG | GGC | 912 |
| Gly | Thr | Leu | Pro | Pro | Ser | Val | Lys | Glu | Ile | Ala | Ile | Ser | Lys | Trp | Gly | |
| | 290 | | | | | 295 | | | | | 300 | | | | | |

```
CAT TTT TAT ATT AAT GGT TAC AAT TTC TTT AGC ACT TTT CCT ATT GAT        960
His Phe Tyr Ile Asn Gly Tyr Asn Phe Phe Ser Thr Phe Pro Ile Asp
305                 310                 315                 320

TGT ATA TCT TTT AAT TTA ACC ACT GGT GAT AGT GGA GCA TTT TGG ACA       1008
Cys Ile Ser Phe Asn Leu Thr Thr Gly Asp Ser Gly Ala Phe Trp Thr
                325                 330                 335

ATT GCT TAC ACA TCG TAC ACT GAC GCA TTA GTA CAA GTT GAA AAC ACA       1056
Ile Ala Tyr Thr Ser Tyr Thr Asp Ala Leu Val Gln Val Glu Asn Thr
            340                 345                 350

GCT ATT AAA AAG GTG ACG TAT TGT AAC AGT CAC ATT AAT AAC ATT AAA       1104
Ala Ile Lys Lys Val Thr Tyr Cys Asn Ser His Ile Asn Asn Ile Lys
        355                 360                 365

TGT TCT CAA CTT ACT GCT AAT TTG CAA AAT GGA TTT TAT CCT GTT GCT       1152
Cys Ser Gln Leu Thr Ala Asn Leu Gln Asn Gly Phe Tyr Pro Val Ala
370                 375                 380

TCA AGT GAA GTT GGT CTT GTC AAT AAG AGT GTT GTG TTA CTA CCT AGT       1200
Ser Ser Glu Val Gly Leu Val Asn Lys Ser Val Val Leu Leu Pro Ser
385                 390                 395                 400

TTC TAT TCA CAT ACC AGT GTT AAT ATA ACT ATT GAT CTT GGT ATG AAG       1248
Phe Tyr Ser His Thr Ser Val Asn Ile Thr Ile Asp Leu Gly Met Lys
                405                 410                 415

CGT AGT GGT TAT GGT CAA CCC ATA GCC TCA ACA TTA                       1284
Arg Ser Gly Tyr Gly Gln Pro Ile Ala Ser Thr Leu
            420                 425
```

(2) INFORMATION FOR SEQ ID NO:43:

(i) SEQUENCE CHARACTERISTICS:
        (A) LENGTH: 428 amino acids
        (B) TYPE: amino acid
        (D) TOPOLOGY: linear (ii) MOLECULE TYPE: protein (xi) SEQUENCE DESCRIPTION: SEQ ID NO:43:

```
Arg Pro Leu Leu Lys His Gly Leu Leu Cys Ile Thr Lys Asn Lys Ile
 1               5                  10                  15

Ile Asp Tyr Asn Thr Phe Thr Ser Ala Gln Trp Ser Ala Ile Cys Leu
                20                  25                  30

Gly Asp Asp Arg Lys Ile Pro Phe Ser Val Ile Pro Thr Gly Asn Gly
            35                  40                  45

Thr Lys Ile Phe Gly Leu Glu Trp Asn Asp Asp Tyr Val Thr Ala Tyr
        50                  55                  60

Ile Ser Asp Arg Ser His His Leu Asn Ile Asn Asn Asn Trp Phe Asn
65                  70                  75                  80

Asn Val Thr Ile Leu Tyr Ser Arg Ser Ser Thr Ala Thr Trp Gln Lys
                85                  90                  95

Ser Ala Ala Tyr Val Tyr Gln Gly Val Ser Asn Phe Thr Tyr Tyr Lys
            100                 105                 110

Leu Asn Asn Thr Asn Gly Leu Lys Ser Tyr Glu Leu Cys Glu Asp Tyr
        115                 120                 125

Glu Cys Cys Thr Gly Tyr Ala Thr Asn Val Phe Ala Pro Thr Val Gly
    130                 135                 140

Gly Tyr Ile Pro Asp Gly Phe Ser Phe Asn Asn Trp Phe Met Leu Thr
145                 150                 155                 160

Asn Ser Ser Thr Phe Val Ser Gly Arg Phe Val Thr Asn Gln Pro Leu
                165                 170                 175

Leu Val Asn Cys Leu Trp Pro Val Pro Ser Leu Gly Val Ala Ala Gln
            180                 185                 190
```

-continued

```
Glu Phe Cys Phe Glu Gly Ala Gln Phe Ser Gln Cys Asn Gly Val Ser
            195                 200                 205

Leu Asn Asn Thr Val Asp Val Ile Arg Phe Asn Leu Asn Phe Thr Thr
        210                 215                 220

Asp Val Gln Ser Gly Met Gly Ala Thr Val Phe Ser Leu Asn Thr Thr
225                 230                 235                 240

Gly Gly Val Ile Leu Glu Ile Ser Cys Tyr Asn Asp Thr Val Ser Glu
                245                 250                 255

Ser Ser Phe Tyr Ser Tyr Gly Glu Ile Ser Phe Gly Val Thr Asp Gly
            260                 265                 270

Pro Arg Tyr Cys Tyr Ala Leu Tyr Asn Gly Thr Ala Leu Lys Tyr Leu
        275                 280                 285

Gly Thr Leu Pro Pro Ser Val Lys Glu Ile Ala Ile Ser Lys Trp Gly
290                 295                 300

His Phe Tyr Ile Asn Gly Tyr Asn Phe Phe Ser Thr Phe Pro Ile Asp
305                 310                 315                 320

Cys Ile Ser Phe Asn Leu Thr Thr Gly Asp Ser Gly Ala Phe Trp Thr
                325                 330                 335

Ile Ala Tyr Thr Ser Tyr Thr Asp Ala Leu Val Gln Val Glu Asn Thr
            340                 345                 350

Ala Ile Lys Lys Val Thr Tyr Cys Asn Ser His Ile Asn Asn Ile Lys
        355                 360                 365

Cys Ser Gln Leu Thr Ala Asn Leu Gln Asn Gly Phe Tyr Pro Val Ala
370                 375                 380

Ser Ser Glu Val Gly Leu Val Asn Lys Ser Val Val Leu Leu Pro Ser
385                 390                 395                 400

Phe Tyr Ser His Thr Ser Val Asn Ile Thr Ile Asp Leu Gly Met Lys
                405                 410                 415

Arg Ser Gly Tyr Gly Gln Pro Ile Ala Ser Thr Leu
            420                 425
```

(2) INFORMATION FOR SEQ ID NO:44:

(i) SEQUENCE CHARACTERISTICS:
        (A) LENGTH: 546 base pairs
        (B) TYPE: nucleic acid
        (C) STRANDEDNESS: double
        (D) TOPOLOGY: unknown (ii) MOLECULE TYPE: DNA (genomic)

(ix) FEATURE:
        (A) NAME/KEY: CDS
        (B) LOCATION: 1..546

(xi) SEQUENCE DESCRIPTION: SEQ ID NO:44:

```
GAT TGT ATA TCT TTT AAT TTA ACC ACT GGT GAT AGT GGA GCA TTT TGG      48
Asp Cys Ile Ser Phe Asn Leu Thr Thr Gly Asp Ser Gly Ala Phe Trp
 1               5                  10                  15

ACA ATT GCT TAC ACA TCG TAC ACT GAC GCA TTA GTA CAA GTT GAA AAC      96
Thr Ile Ala Tyr Thr Ser Tyr Thr Asp Ala Leu Val Gln Val Glu Asn
                20                  25                  30

ACA GCT ATT AAA AAG GTG ACG TAT TGT AAC AGT CAC ATT AAT AAC ATT     144
Thr Ala Ile Lys Lys Val Thr Tyr Cys Asn Ser His Ile Asn Asn Ile
            35                  40                  45

AAA TGT TCT CAA CTT ACT GCT AAT TTG CAA AAT GGA TTT TAT CCT GTT     192
Lys Cys Ser Gln Leu Thr Ala Asn Leu Gln Asn Gly Phe Tyr Pro Val
        50                  55                  60
```

```
GCT TCA AGT GAA GTT GGT CTT GTC AAT AAG AGT GTT GTG TTA CTA CCT         240
Ala Ser Ser Glu Val Gly Leu Val Asn Lys Ser Val Val Leu Leu Pro
 65                  70                  75                  80

AGT TTC TAT TCA CAT ACC AGT GTT AAT ATA ACT ATT GAT CTT GGT ATG         288
Ser Phe Tyr Ser His Thr Ser Val Asn Ile Thr Ile Asp Leu Gly Met
                 85                  90                  95

AAG CGT AGT GGT TAT GGT CAA CCC ATA GCC TCA ACA TTA AGT AAC ATC         336
Lys Arg Ser Gly Tyr Gly Gln Pro Ile Ala Ser Thr Leu Ser Asn Ile
            100                 105                 110

ACA CTA CCA ATG CAG GAT AAT AAC ACC GAT GTG TAC TGC ATT CGT TCT         384
Thr Leu Pro Met Gln Asp Asn Asn Thr Asp Val Tyr Cys Ile Arg Ser
        115                 120                 125

AAC CAA TTT TCA GTT TAC GTT CAT TCC ACT TGT AAA AGT TCT TTA TGG         432
Asn Gln Phe Ser Val Tyr Val His Ser Thr Cys Lys Ser Ser Leu Trp
    130                 135                 140

GAC GAT GTG TTT AAT TCC GAC TGC ACA GAT GTT TTA TAT GCT ACA GCT         480
Asp Asp Val Phe Asn Ser Asp Cys Thr Asp Val Leu Tyr Ala Thr Ala
145                 150                 155                 160

GTT ATA AAA ACT GGT ACT TGT CCT TTC TCG TTT GAT AAA TTG AAC AAT         528
Val Ile Lys Thr Gly Thr Cys Pro Phe Ser Phe Asp Lys Leu Asn Asn
                165                 170                 175

TAC TTA ACT TTT AAC AAG                                                 546
Tyr Leu Thr Phe Asn Lys
            180

(2) INFORMATION FOR SEQ ID NO:45:

(i) SEQUENCE CHARACTERISTICS:
        (A) LENGTH: 182 amino acids
        (B) TYPE: amino acid
        (D) TOPOLOGY: linear (ii) MOLECULE TYPE: protein (xi) SEQUENCE DESCRIPTION: SEQ ID NO:45:

Asp Cys Ile Ser Phe Asn Leu Thr Thr Gly Asp Ser Gly Ala Phe Trp
  1               5                  10                  15

Thr Ile Ala Tyr Thr Ser Tyr Thr Asp Ala Leu Val Gln Val Glu Asn
             20                  25                  30

Thr Ala Ile Lys Lys Val Thr Tyr Cys Asn Ser His Ile Asn Asn Ile
         35                  40                  45

Lys Cys Ser Gln Leu Thr Ala Asn Leu Gln Asn Gly Phe Tyr Pro Val
     50                  55                  60

Ala Ser Ser Glu Val Gly Leu Val Asn Lys Ser Val Val Leu Leu Pro
 65                  70                  75                  80

Ser Phe Tyr Ser His Thr Ser Val Asn Ile Thr Ile Asp Leu Gly Met
                 85                  90                  95

Lys Arg Ser Gly Tyr Gly Gln Pro Ile Ala Ser Thr Leu Ser Asn Ile
            100                 105                 110

Thr Leu Pro Met Gln Asp Asn Asn Thr Asp Val Tyr Cys Ile Arg Ser
        115                 120                 125

Asn Gln Phe Ser Val Tyr Val His Ser Thr Cys Lys Ser Ser Leu Trp
    130                 135                 140

Asp Asp Val Phe Asn Ser Asp Cys Thr Asp Val Leu Tyr Ala Thr Ala
145                 150                 155                 160

Val Ile Lys Thr Gly Thr Cys Pro Phe Ser Phe Asp Lys Leu Asn Asn
                165                 170                 175

Tyr Leu Thr Phe Asn Lys
            180
```

(2) INFORMATION FOR SEQ ID NO:46:

(i) SEQUENCE CHARACTERISTICS:
        (A) LENGTH: 38 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:46:

TAAATAGGCC TTTAGTGGAC ATGCACTTTT TCAATTGG        38

(2) INFORMATION FOR SEQ ID NO:47:

(i) SEQUENCE CHARACTERISTICS:
        (A) LENGTH: 39 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:47:

TTAGTAGGCC TGTCGAGGCT ATGGGTTGAC CATAACCAC        39

(2) INFORMATION FOR SEQ ID NO:48:

(i) SEQUENCE CHARACTERISTICS:
        (A) LENGTH: 37 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:48:

CAGATCCCGG GTGTACAATC TGGTATGGGT GCTACAG        37

(2) INFORMATION FOR SEQ ID NO:49:

(i) SEQUENCE CHARACTERISTICS:
        (A) LENGTH: 39 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:49:

GTGCCCCCGG GTATGATTGT GCTCGTAACT TGCCTCTTG        39

(2) INFORMATION FOR SEQ ID NO:50:

(i) SEQUENCE CHARACTERISTICS:
        (A) LENGTH: 43 base pairs
        (B) TYPE: nucleic acid
        (C) STRANDEDNESS: single
        (D) TOPOLOGY: unknown (ii) MOLECULE TYPE: DNA (genomic)

(xi) SEQUENCE DESCRIPTION: SEQ ID NO:50:

AGCACCCATA CCAGATTGTA CATCTGCAGT GAAATTAAGA TTG        43

(2) INFORMATION FOR SEQ ID NO:51:

(i) SEQUENCE CHARACTERISTICS:
        (A) LENGTH: 128 amino acids
        (B) TYPE: amino acid
        (D) TOPOLOGY: unknown (ii) MOLECULE TYPE: protein (xi) SEQUENCE DESCRIPTION: SEQ ID NO:51:

```
Met Ile Val Leu Val Thr Cys Leu Leu Phe Ser Tyr Asn Ser Val Ile
1               5                   10                  15

Cys Thr Ser Asn Asn Asp Cys Val Gln Val Asn Val Thr Gln Leu Pro
                20                  25                  30

Gly Asn Glu Asn Ile Ile Lys Asp Phe Leu Phe His Thr Phe Lys Glu
            35                  40                  45

Glu Gly Ser Val Val Val Gly Tyr Tyr Pro Thr Glu Val Trp Tyr
        50                  55                  60

Asn Cys Ser Arg Ser Ala Thr Thr Ala Tyr Lys Asp Phe Ser Asn
65                  70                  75                  80

Ile His Ala Phe Tyr Phe Asp Met Glu Ala Met Glu Asn Ser Thr Gly
                85                  90                  95

Asn Ala Arg Gly Lys Pro Leu Leu Val His Val His Gly Asp Pro Val
            100                 105                 110

Ser Ile Ile Ile Tyr Ile Ser Ala Tyr Arg Asp Asp Val Gln Gly Arg
            115                 120                 125
```

(2) INFORMATION FOR SEQ ID NO:52:

(i) SEQUENCE CHARACTERISTICS:
        (A) LENGTH: 1101 amino acids
        (B) TYPE: amino acid
        (D) TOPOLOGY: unknown (ii) MOLECULE TYPE: protein (xi) SEQUENCE DESCRIPTION: SEQ ID NO:52:

```
Asp Val Gln Ser Gly Met Gly Ala Thr Val Phe Ser Leu Asn Thr Thr
1               5                   10                  15

Gly Gly Val Ile Leu Glu Ile Ser Cys Tyr Asn Asp Thr Val Ser Glu
                20                  25                  30

Ser Ser Phe Tyr Ser Tyr Gly Glu Ile Ser Phe Gly Val Thr Asp Gly
            35                  40                  45

Pro Arg Tyr Cys Tyr Ala Leu Tyr Asn Gly Thr Ala Leu Lys Tyr Leu
        50                  55                  60

Gly Thr Leu Pro Pro Ser Val Lys Glu Ile Ala Ile Ser Lys Trp Gly
65                  70                  75                  80

His Phe Tyr Ile Asn Gly Tyr Asn Phe Phe Ser Thr Phe Pro Ile Asp
                85                  90                  95

Cys Ile Ser Phe Asn Leu Thr Thr Gly Asp Ser Gly Ala Phe Trp Thr
            100                 105                 110

Ile Ala Tyr Thr Ser Tyr Thr Asp Ala Leu Val Gln Val Glu Asn Thr
            115                 120                 125

Ala Ile Lys Lys Val Thr Tyr Cys Asn Ser His Ile Asn Asn Ile Lys
        130                 135                 140

Cys Ser Gln Leu Thr Ala Asn Leu Gln Asn Gly Phe Tyr Pro Val Ala
145                 150                 155                 160

Ser Ser Glu Val Gly Leu Val Asn Lys Ser Val Val Leu Leu Pro Ser
                165                 170                 175

Phe Tyr Ser His Thr Ser Val Asn Ile Thr Ile Asp Leu Gly Met Lys
```

-continued

```
            180                 185                 190
Arg Ser Gly Tyr Gly Gln Pro Ile Ala Ser Thr Leu Ser Asn Ile Thr
        195                 200                 205
Leu Pro Met Gln Asp Asn Asn Thr Asp Val Tyr Cys Ile Arg Ser Asn
210                 215                 220
Gln Phe Ser Val Tyr Val His Ser Thr Cys Lys Ser Ser Leu Trp Asp
225                 230                 235                 240
Asp Val Phe Asn Ser Asp Cys Thr Asp Val Leu Tyr Ala Thr Ala Val
                245                 250                 255
Ile Lys Thr Gly Thr Cys Pro Phe Ser Phe Asp Lys Leu Asn Asn Tyr
                260                 265                 270
Leu Thr Phe Asn Lys Phe Cys Leu Ser Leu Asn Pro Val Gly Ala Asn
            275                 280                 285
Cys Lys Phe Asp Val Ala Ala Arg Thr Arg Thr Asn Glu Gln Val Val
290                 295                 300
Arg Ser Leu Tyr Val Ile Tyr Glu Glu Gly Asp Asn Ile Val Gly Val
305                 310                 315                 320
Pro Ser Asp Asn Ser Gly Leu His Asp Leu Ser Val Leu His Leu Asp
                325                 330                 335
Ser Cys Thr Asp Tyr Asn Ile Tyr Gly Arg Thr Gly Val Gly Ile Ile
                340                 345                 350
Arg Gln Thr Asn Ser Thr Leu Leu Ser Gly Leu Tyr Tyr Thr Ser Leu
            355                 360                 365
Ser Gly Asp Leu Leu Gly Phe Lys Asn Val Ser Asp Gly Val Ile Tyr
        370                 375                 380
Ser Val Thr Pro Cys Asp Val Ser Ala Gln Ala Ala Val Ile Asp Gly
385                 390                 395                 400
Ala Ile Val Gly Ala Met Thr Ser Ile Asn Ser Glu Met Leu Gly Leu
                405                 410                 415
Thr His Trp Thr Thr Thr Pro Asn Phe Tyr Tyr Ser Ile Tyr Asn
                420                 425                 430
Tyr Thr Asn Glu Arg Thr Arg Gly Thr Ala Ile Asp Ser Asn Asp Val
            435                 440                 445
Asp Cys Glu Pro Ile Ile Thr Tyr Ser Asn Ile Gly Val Cys Lys Asn
450                 455                 460
Gly Ala Leu Val Phe Ile Asn Val Thr His Ser Asp Gly Asp Val Gln
465                 470                 475                 480
Pro Ile Ser Thr Gly Asn Val Thr Ile Pro Thr Asn Phe Thr Ile Ser
                485                 490                 495
Val Gln Val Glu Tyr Ile Gln Val Tyr Thr Thr Pro Val Ser Ile Asp
            500                 505                 510
Cys Ser Arg Tyr Val Cys Asn Gly Asn Pro Arg Cys Asn Lys Leu Leu
        515                 520                 525
Thr Gln Tyr Val Ser Ala Cys Gln Thr Ile Glu Gln Ala Leu Ala Met
        530                 535                 540
Gly Ala Arg Leu Glu Asn Met Glu Ile Asp Ser Met Leu Phe Val Ser
545                 550                 555                 560
Glu Asn Ala Leu Lys Leu Ala Ser Val Glu Ala Phe Asn Ser Thr Glu
                565                 570                 575
Thr Leu Asp Pro Ile Tyr Lys Glu Trp Pro Asn Ile Gly Gly Ser Trp
            580                 585                 590
Leu Gly Gly Leu Lys Asp Ile Leu Pro Ser His Asn Ser Lys Arg Lys
        595                 600                 605
```

```
Tyr Arg Ser Ala Ile Glu Asp Leu Leu Phe Asp Lys Val Val Thr Ser
    610                 615                 620

Gly Leu Gly Thr Val Asp Glu Asp Tyr Lys Arg Cys Thr Gly Gly Tyr
625                 630                 635                 640

Asp Ile Ala Asp Leu Val Cys Ala Gln Tyr Tyr Asn Gly Ile Met Val
                645                 650                 655

Leu Pro Gly Val Ala Asn Asp Lys Met Ala Met Tyr Thr Ala Ser
                660                 665                 670

Leu Ala Gly Gly Ile Thr Leu Gly Ala Leu Gly Gly Ala Val Ser
            675                 680                 685

Ile Pro Phe Ala Ile Ala Val Gln Ala Arg Leu Asn Tyr Val Ala Leu
    690                 695                 700

Gln Thr Asp Val Leu Ser Lys Asn Gln Gln Ile Leu Ala Asn Ala Phe
705                 710                 715                 720

Asn Gln Ala Ile Gly Asn Ile Thr Gln Ala Phe Gly Lys Val Asn Asp
                725                 730                 735

Ala Ile His Gln Thr Ser Gln Gly Leu Ala Thr Val Ala Lys Ala Leu
                740                 745                 750

Ala Lys Val Gln Asp Val Val Asn Thr Gln Gly Gln Ala Leu Ser His
            755                 760                 765

Leu Thr Val Gln Leu Gln Asn Asn Phe Gln Ala Ile Ser Ser Ser Ile
770                 775                 780

Ser Asp Ile Tyr Asn Arg Leu Asp Glu Leu Ser Ala Asp Ala Gln Val
785                 790                 795                 800

Asp Arg Leu Ile Thr Gly Arg Leu Thr Ala Leu Asn Ala Phe Val Ser
                805                 810                 815

Gln Thr Leu Thr Arg Gln Ala Glu Val Arg Ala Ser Arg Gln Leu Ala
                820                 825                 830

Lys Asp Lys Val Asn Glu Cys Val Arg Ser Gln Ser Gln Arg Phe Gly
            835                 840                 845

Phe Cys Gly Asn Gly Thr His Leu Phe Ser Leu Ala Asn Ala Ala Pro
850                 855                 860

Asn Gly Met Ile Phe Phe His Thr Val Leu Leu Pro Thr Ala Tyr Glu
865                 870                 875                 880

Thr Val Thr Ala Trp Ser Gly Ile Cys Ala Ser Asp Gly Asp Arg Thr
                885                 890                 895

Phe Gly Leu Val Val Lys Asp Val Gln Leu Thr Leu Phe Arg Asn Leu
                900                 905                 910

Asp Asp Lys Phe Tyr Leu Thr Pro Arg Thr Met Tyr Gln Pro Arg Val
            915                 920                 925

Ala Thr Ser Ser Asp Phe Val Gln Ile Glu Gly Cys Asp Val Leu Phe
930                 935                 940

Val Asn Ala Thr Val Ile Asp Leu Pro Ser Ile Ile Pro Asp Tyr Ile
945                 950                 955                 960

Asp Ile Asn Gln Thr Val Gln Asp Ile Leu Glu Asn Phe Arg Pro Asn
                965                 970                 975

Trp Thr Val Pro Glu Leu Pro Leu Asp Ile Phe Asn Ala Thr Tyr Leu
                980                 985                 990

Asn Leu Thr Gly Glu Ile Asn Asp Leu Glu Phe Arg Ser Glu Lys Leu
            995                 1000                1005

His Asn Thr Thr Val Glu Leu Ala Ile Leu Ile Asp Asn Ile Asn Asn
    1010                1015                1020
```

```
Thr Leu Val Asn Leu Glu Trp Leu Asn Arg Ile Glu Thr Tyr Val Lys
1025                1030                1035                1040

Trp Pro Trp Tyr Val Trp Leu Leu Ile Gly Leu Val Val Ile Phe Cys
                1045                1050                1055

Ile Pro Ile Leu Leu Phe Cys Cys Cys Ser Thr Gly Cys Cys Gly Cys
                1060                1065                1070

Ile Gly Cys Leu Gly Ser Cys Cys His Ser Ile Cys Ser Arg Arg Arg
            1075                1080                1085

Phe Glu Ser Tyr Glu Pro Ile Glu Lys Val His Val His
1090                1095                1100
```

(2) INFORMATION FOR SEQ ID NO:53:

(i) SEQUENCE CHARACTERISTICS:
        (A) LENGTH: 362 amino acids
        (B) TYPE: amino acid
        (D) TOPOLOGY: unknown (ii) MOLECULE TYPE: protein (xi) SEQUENCE DESCRIPTION: SEQ ID NO:53:

```
Met Ile Val Leu Val Thr Cys Leu Leu Phe Ser Tyr Asn Ser Val Ile
1               5                   10                  15

Cys Thr Ser Asn Asn Asp Cys Val Gln Val Asn Val Thr Gln Leu Pro
                20                  25                  30

Gly Asn Glu Asn Ile Ile Lys Asp Phe Leu Phe His Thr Phe Lys Glu
            35                  40                  45

Glu Gly Ser Val Val Val Gly Gly Tyr Tyr Pro Thr Glu Val Trp Tyr
50                  55                  60

Asn Cys Ser Arg Ser Ala Thr Thr Thr Ala Tyr Lys Asp Phe Ser Asn
65                  70                  75                  80

Ile His Ala Phe Tyr Phe Asp Met Glu Ala Met Glu Asn Ser Thr Gly
                85                  90                  95

Asn Ala Arg Gly Lys Pro Leu Leu Val His Val His Gly Asp Pro Val
            100                 105                 110

Ser Ile Ile Ile Tyr Ile Ser Ala Tyr Arg Asp Asp Val Gln Gly Arg
        115                 120                 125

Pro Leu Leu Lys His Gly Leu Leu Cys Ile Thr Lys Asn Lys Ile Ile
        130                 135                 140

Asp Tyr Asn Thr Phe Thr Ser Ala Gln Trp Ser Ala Ile Cys Leu Gly
145                 150                 155                 160

Asp Asp Arg Lys Ile Pro Phe Ser Val Ile Pro Thr Gly Asn Gly Thr
                165                 170                 175

Lys Ile Phe Gly Leu Glu Trp Asn Asp Asp Tyr Val Thr Ala Tyr Ile
            180                 185                 190

Ser Asp Arg Ser His His Leu Asn Ile Asn Asn Asn Trp Phe Asn Asn
        195                 200                 205

Val Thr Ile Leu Tyr Ser Arg Ser Ser Thr Ala Thr Trp Gln Lys Ser
210                 215                 220

Ala Ala Tyr Val Tyr Gln Gly Val Ser Asn Phe Thr Tyr Tyr Lys Leu
225                 230                 235                 240

Asn Asn Thr Asn Gly Leu Lys Ser Tyr Glu Leu Cys Glu Asp Tyr Glu
                245                 250                 255

Cys Cys Thr Gly Tyr Ala Thr Asn Val Phe Ala Pro Thr Val Gly Gly
            260                 265                 270

Tyr Ile Pro Asp Gly Phe Ser Phe Asn Asn Trp Phe Met Leu Thr Asn
```

```
                275                 280                 285
Ser Ser Thr Phe Val Ser Gly Arg Phe Val Thr Asn Gln Pro Leu Leu
290                 295                 300

Val Asn Cys Leu Trp Pro Val Pro Ser Leu Gly Val Ala Ala Gln Glu
305                 310                 315                 320

Phe Cys Phe Glu Gly Ala Gln Phe Ser Gln Cys Asn Gly Val Ser Leu
                    325                 330                 335

Asn Asn Thr Val Asp Val Ile Arg Phe Asn Leu Asn Phe Thr Thr Asp
                340                 345                 350

Val Gln Ser Gly Met Gly Ala Thr Val Phe
                355                 360
```

(2) INFORMATION FOR SEQ ID NO:54:

(i) SEQUENCE CHARACTERISTICS:
        (A) LENGTH: 1101 amino acids
        (B) TYPE: amino acid
        (D) TOPOLOGY: unknown (ii) MOLECULE TYPE: protein (xi) SEQUENCE DESCRIPTION: SEQ ID NO:54:

```
Ala Ala Tyr Val Tyr Gln Gly Val Ser Asn Phe Thr Tyr Tyr Lys Leu
1               5                   10                  15

Asn Asn Thr Asn Gly Leu Lys Ser Tyr Glu Leu Cys Glu Asp Tyr Glu
                20                  25                  30

Cys Cys Thr Gly Tyr Ala Thr Asn Val Phe Ala Pro Thr Val Gly Gly
                35                  40                  45

Tyr Ile Pro Asp Gly Phe Ser Phe Asn Asn Trp Phe Met Leu Thr Asn
50                  55                  60

Ser Ser Thr Phe Val Ser Gly Arg Phe Val Thr Asn Gln Pro Leu Leu
65                  70                  75                  80

Val Asn Cys Leu Trp Pro Val Pro Ser Leu Gly Val Ala Ala Gln Glu
                85                  90                  95

Phe Cys Phe Glu Gly Ala Gln Phe Ser Gln Cys Asn Gly Val Ser Leu
                100                 105                 110

Asn Asn Thr Val Asp Val Ile Arg Phe Asn Leu Asn Phe Thr Thr Asp
                115                 120                 125

Val Gln Ser Gly Met Gly Ala Thr Val Phe Ser Leu Asn Thr Thr Gly
                130                 135                 140

Gly Val Ile Leu Glu Ile Ser Cys Tyr Asn Asp Thr Val Ser Glu Ser
145                 150                 155                 160

Ser Phe Tyr Ser Tyr Gly Glu Ile Ser Phe Gly Val Thr Asp Gly Pro
                165                 170                 175

Arg Tyr Cys Tyr Ala Leu Tyr Asn Gly Thr Ala Leu Lys Tyr Leu Gly
                180                 185                 190

Thr Leu Pro Pro Ser Val Lys Glu Ile Ala Ile Ser Lys Trp Gly His
                195                 200                 205

Phe Tyr Ile Asn Gly Tyr Asn Phe Phe Ser Thr Phe Pro Ile Asp Cys
                210                 215                 220

Ile Ser Phe Asn Leu Thr Thr Gly Asp Ser Gly Ala Phe Trp Thr Ile
225                 230                 235                 240

Ala Tyr Thr Ser Tyr Thr Asp Ala Leu Val Gln Val Glu Asn Thr Ala
                245                 250                 255

Ile Lys Lys Val Thr Tyr Cys Asn Ser His Ile Asn Asn Ile Lys Cys
                260                 265                 270
```

-continued

```
Ser Gln Leu Thr Ala Asn Leu Gln Asn Gly Phe Tyr Pro Val Ala Ser
    275                 280                 285

Ser Glu Val Gly Leu Val Asn Lys Ser Val Val Leu Leu Pro Ser Phe
    290                 295                 300

Tyr Ser His Thr Ser Val Asn Ile Thr Ile Asp Leu Gly Met Lys Arg
305                 310                 315                 320

Ser Gly Tyr Gly Gln Pro Ile Ala Ser Thr Leu Ser Asn Ile Thr Leu
                325                 330                 335

Pro Met Gln Asp Asn Asn Thr Asp Val Tyr Cys Ile Arg Ser Asn Gln
            340                 345                 350

Phe Ser Val Tyr Val His Ser Thr Cys Lys Ser Ser Leu Trp Asp Asp
        355                 360                 365

Val Phe Asn Ser Asp Cys Thr Asp Val Leu Tyr Ala Thr Ala Val Ile
    370                 375                 380

Lys Thr Gly Thr Cys Pro Phe Ser Phe Asp Lys Leu Asn Asn Tyr Leu
385                 390                 395                 400

Thr Phe Asn Lys Phe Cys Leu Ser Leu Asn Pro Val Gly Ala Asn Cys
                405                 410                 415

Lys Phe Asp Val Ala Ala Arg Thr Arg Thr Asn Glu Gln Val Val Arg
            420                 425                 430

Ser Leu Tyr Val Ile Tyr Glu Glu Gly Asp Asn Ile Val Gly Val Pro
        435                 440                 445

Ser Asp Asn Ser Gly Leu His Asp Leu Ser Val Leu His Leu Asp Ser
    450                 455                 460

Cys Thr Asp Tyr Asn Ile Tyr Gly Arg Thr Gly Val Gly Ile Ile Arg
465                 470                 475                 480

Gln Thr Asn Ser Thr Leu Leu Ser Gly Leu Tyr Tyr Thr Ser Leu Ser
                485                 490                 495

Gly Asp Leu Leu Gly Phe Lys Asn Val Ser Asp Gly Val Ile Tyr Ser
            500                 505                 510

Val Thr Pro Cys Asp Val Ser Ala Gln Ala Ala Val Ile Asp Gly Ala
        515                 520                 525

Ile Val Gly Ala Met Thr Ser Ile Asn Ser Glu Met Leu Gly Leu Thr
    530                 535                 540

His Trp Thr Thr Thr Pro Asn Phe Tyr Tyr Tyr Ser Ile Tyr Asn Tyr
545                 550                 555                 560

Thr Asn Glu Arg Thr Arg Gly Thr Ala Ile Asp Ser Asn Asp Val Asp
                565                 570                 575

Cys Glu Pro Ile Ile Thr Tyr Ser Asn Ile Gly Val Cys Lys Asn Gly
            580                 585                 590

Ala Leu Val Phe Ile Asn Val Thr His Ser Asp Gly Asp Val Gln Pro
        595                 600                 605

Ile Ser Thr Gly Asn Val Thr Ile Pro Thr Asn Phe Thr Ile Ser Val
    610                 615                 620

Gln Val Glu Tyr Ile Gln Val Tyr Thr Thr Pro Val Ser Ile Asp Cys
625                 630                 635                 640

Ser Arg Tyr Val Cys Asn Gly Asn Pro Arg Cys Asn Lys Leu Leu Thr
                645                 650                 655

Gln Tyr Val Ser Ala Cys Gln Thr Ile Glu Gln Ala Leu Ala Met Gly
            660                 665                 670

Ala Arg Leu Glu Asn Met Glu Ile Asp Ser Met Leu Phe Val Ser Glu
        675                 680                 685
```

```
Asn Ala Leu Lys Leu Ala Ser Val Glu Ala Phe Asn Ser Thr Glu Thr
    690                 695                 700
Leu Asp Pro Ile Tyr Lys Glu Trp Pro Asn Ile Gly Gly Ser Trp Leu
705                 710                 715                 720
Gly Gly Leu Lys Asp Ile Leu Pro Ser His Asn Ser Lys Arg Lys Tyr
                    725                 730                 735
Arg Ser Ala Ile Glu Asp Leu Leu Phe Asp Lys Val Val Thr Ser Gly
                740                 745                 750
Leu Gly Thr Val Asp Glu Asp Tyr Lys Arg Cys Thr Gly Gly Tyr Asp
            755                 760                 765
Ile Ala Asp Leu Val Cys Ala Gln Tyr Tyr Asn Gly Ile Met Val Leu
        770                 775                 780
Pro Gly Val Ala Asn Asp Lys Met Ala Met Tyr Thr Ala Ser Leu
785                 790                 795                 800
Ala Gly Gly Ile Thr Leu Gly Ala Leu Gly Gly Ala Val Ser Ile
                805                 810                 815
Pro Phe Ala Ile Ala Val Gln Ala Arg Leu Asn Tyr Val Ala Leu Gln
                    820                 825                 830
Thr Asp Val Leu Ser Lys Asn Gln Gln Ile Leu Ala Asn Ala Phe Asn
                835                 840                 845
Gln Ala Ile Gly Asn Ile Thr Gln Ala Phe Gly Lys Val Asn Asp Ala
    850                 855                 860
Ile His Gln Thr Ser Gln Gly Leu Ala Thr Val Ala Lys Ala Leu Ala
865                 870                 875                 880
Lys Val Gln Asp Val Val Asn Thr Gln Gly Gln Ala Leu Ser His Leu
                885                 890                 895
Thr Val Gln Leu Gln Asn Asn Phe Gln Ala Ile Ser Ser Ser Ile Ser
                900                 905                 910
Asp Ile Tyr Asn Arg Leu Asp Glu Leu Ser Ala Asp Ala Gln Val Asp
        915                 920                 925
Arg Leu Ile Thr Gly Arg Leu Thr Ala Leu Asn Ala Phe Val Ser Gln
    930                 935                 940
Thr Leu Thr Arg Gln Ala Glu Val Arg Ala Ser Arg Gln Leu Ala Lys
945                 950                 955                 960
Asp Lys Val Asn Glu Cys Val Arg Ser Gln Ser Gln Arg Phe Gly Phe
                965                 970                 975
Cys Gly Asn Gly Thr His Leu Phe Ser Leu Ala Asn Ala Ala Pro Asn
                980                 985                 990
Gly Met Ile Phe Phe His Thr Val Leu Leu Pro Thr Ala Tyr Glu Thr
                995                 1000                1005
Val Thr Ala Trp Ser Gly Ile Cys Ala Ser Asp Gly Asp Arg Thr Phe
    1010                1015                1020
Gly Leu Val Val Lys Asp Val Gln Leu Thr Leu Phe Arg Asn Leu Asp
1025                1030                1035                1040
Asp Lys Phe Tyr Leu Thr Pro Arg Thr Met Tyr Gln Pro Arg Val Ala
                1045                1050                1055
Thr Ser Ser Asp Phe Val Gln Ile Glu Gly Cys Asp Val Leu Phe Val
                1060                1065                1070
Asn Ala Thr Val Ile Asp Leu Pro Ser Ile Ile Pro Asp Tyr Ile Asp
                1075                1080                1085
Ile Asn Gln Thr Val Gln Asp Ile Leu Glu Asn Phe Arg
    1090                1095                1100
```

(2) INFORMATION FOR SEQ ID NO:55:

(i) SEQUENCE CHARACTERISTICS:
        (A) LENGTH: 701 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:55:

```
TCAACCATTA TTGGTTAATT GTTTGTGGCC AGTGCCCAGT CTTGGTGTCG CAGCACAAGA    60
ATTTTGTTTT GAAGGTGCGC AGTTTAGCCA ATGTAATGGT GTGTCTTTAA ACAATACAGT   120
GGATGTCATT AGATTCAACC TTAATTTTAC CACAGATGTA CAATCTGGTA TGGGTGCTAC   180
AGTATTTTCA CTGAATACAA CAGGTGGTGT CATTCTTGAG ATTTCTTGTT ATAATGATAC   240
AGTGAGTGAG TCAAGTTTCT ACAGTTATGG TGAAATTTCA TTCGGCGTAA CTGATGGACC   300
GCGTTACTGT TACGCACTCT ATAATGGCAC GGCTCTTAAG TATTTAGGAA CATTACCACC   360
TAGTGTCAAG GAAATTGCTA TTAGTAAGTG GGGCCATTTT TATATTAATG GTTACAATTT   420
CTTTAGCACT TTTCCTATTG ATTGTATATC TTTTAATTTA ACCACTGGTG ATAGTGGAGC   480
ATTTTGGACA ATTGCTTACA CATCGTACAC TGACGCATTA GTACAAGTTG AAAACACAGC   540
TATTAAAAAG GTGACGTATT GTAACAGTCA CATTAATAAC ATTAAATGTT CTCAACTTAC   600
TGCTAATTTG CAAAATGGAT TTTATCCTGT TGCTTCAAGT GAAGTTGGTC TTGTCAATAA   660
GAGTGTTGTG TTACTACCTA GTTTCTATTC ACATACCAGT G                      701
```

(2) INFORMATION FOR SEQ ID NO:56:

(i) SEQUENCE CHARACTERISTICS:
        (A) LENGTH: 1401 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:56:

```
AGCACCGGTA ATGTCACGAT ACCTACAAAT TTTACCATAT CTGTGCAAGT TGAGTACATT    60
CAGGTTTACA CTACACCGGT GTCAATAGAT TGTTCAAGGT ACGTTTGCAA TGGTAACCCT   120
AGATGCAATA AATTGTTAAC GCAATACGTT TCTGCATGTC AAACTATTGA GCAAGCACTT   180
GCAATGGGTG CCAGACTTGA AAACATGGAG ATTGATTCCA TGTTGTTTGT TTCGGAAAAT   240
GCCCTTAAAT TGGCATCTGT TGAAGCATTC AATAGTACGG AAACTTTAGA TCCTATTTAC   300
AAAGAATGGC CTAACATTGG TGGTTCTTGG CTAGGAGGTT TAAAAGACAT ATTGCCATCT   360
CACAACAGCA AACGTAAGTA CCGGTCGGCT ATAGAAGATT TGCTTTTTGA TAAGGTTGTA   420
ACATCTGGCT TAGGTACAGT TGATGAAGAT TATAAACGTT GTACAGGTGG TTATGACATA   480
GCTGACTTAG TGTGTGCACA ATATTACAAT GGCATCATGG TGCTACCTGG TGTAGCTAAT   540
GATGACAAGA TGGCTATGTA CACTGCATCT CTTGCAGGTG GTATAACATT AGGTGCACTT   600
GGTGGTGGCG CAGTGTCTAT ACCTTTTGCA ATAGCAGTTC AAGCCAGACT TAATTATGTT   660
GCTCTACAAA CTGATGTATT GAGCAAGAAC CAGCAGATCC TGGCTAATGC TTTCAATCAA   720
GCTATTGGTA ACATTACACA GGCATTTGGT AAGGTTAATG ATGCTATACA TCAAACGTCA   780
CAAGGTCTTG CTACTGTTGC TAAAGCATTG GCAAAAGTGC AAGATGTTGT TAACACACAA   840
GGGCAAGCTT TAAGCCACCT AACAGTACAA TTGCAAAATA ATTTCCAAGC CATTAGTAGT   900
```

-continued

```
TCCATTAGTG ACATTTATAA CAGGCTTGAT GAATTGAGTG CTGATGCACA AGTTGACAGG      960

CTGATTACAG GAAGACTTAC AGCACTTAAT GCATTTGTGT CTCAGACTTT AACCAGACAA     1020

GCAGAGGTTA GGGCTAGCAG ACAGCTTGCT AAAGACAAGG TAAATGAATG CGTTAGGTCT     1080

CAATCTCAGA GATTTGGATT CTGTGGTAAT GGTACACATT TATTTTCACT TGCAAATGCA     1140

GCACCAAATG GCATGATCTT CTTTCACACA GTGCTATTAC AACAGCTTA  TGAAACCGTG     1200

ACGGCCTGGT CAGGTATTTG TGCATCAGAT GGCGATCGTA CTTTTGGACT TGTTGTTAAG     1260

GATGTCCAGT TGACGCTGTT TCGCAATCTA GATGACAAAT TCTATTTGAC TCCCAGAACT     1320

ATGTATCAGC CTAGAGTTGC AACTAGTTCT GATTTTGTTC AAATTGAAGG ATGTGATGTG     1380

TTGTTTGTTA ATGCAACTGT A                                               1401
```

(2) INFORMATION FOR SEQ ID NO:57:

(i) SEQUENCE CHARACTERISTICS:
        (A) LENGTH: 250 amino acids
        (B) TYPE: amino acid
        (D) TOPOLOGY: unknown (ii) MOLECULE TYPE: protein (xi) SEQUENCE DESCRIPTION: SEQ ID NO:57:

```
Met Ile Val Leu Val Thr Cys Leu Leu Phe Ser Tyr Asn Ser Val Ile
1               5                   10                  15

Cys Thr Ser Asn Asn Asp Cys Val Gln Val Asn Val Thr Gln Leu Pro
            20                  25                  30

Gly Asn Glu Asn Ile Ile Lys Asp Phe Leu Phe His Thr Phe Lys Glu
        35                  40                  45

Glu Gly Ser Val Val Val Gly Tyr Tyr Pro Thr Glu Val Trp Tyr
    50                  55                  60

Asn Cys Ser Arg Ser Ala Thr Thr Thr Ala Tyr Lys Asp Phe Ser Asn
65                  70                  75                  80

Ile His Ala Phe Tyr Phe Asp Met Glu Ala Met Glu Asn Ser Thr Gly
                85                  90                  95

Asn Ala Arg Gly Lys Pro Leu Leu Val His Val His Gly Asp Pro Val
            100                 105                 110

Ser Ile Ile Ile Tyr Ile Ser Ala Tyr Arg Asp Asp Val Gln Gly Arg
        115                 120                 125

Pro Leu Leu Lys His Gly Leu Leu Cys Ile Thr Lys Asn Lys Ile Ile
    130                 135                 140

Asp Tyr Asn Thr Phe Thr Ser Ala Gln Trp Ser Ala Ile Cys Leu Gly
145                 150                 155                 160

Asp Asp Arg Lys Ile Pro Phe Ser Val Ile Pro Thr Gly Asn Gly Thr
                165                 170                 175

Lys Ile Phe Gly Leu Glu Trp Asn Asp Asp Tyr Val Thr Ala Tyr Ile
            180                 185                 190

Ser Asp Arg Ser His His Leu Asn Ile Asn Asn Asn Trp Phe Asn Asn
        195                 200                 205

Val Thr Ile Leu Tyr Ser Arg Ser Ser Thr Ala Thr Trp Gln Lys Ser
    210                 215                 220

Ala Ala Tyr Val Tyr Gln Gly Val Ser Asn Phe Thr Tyr Tyr Lys Leu
225                 230                 235                 240

Asn Asn Thr Asn Gly Leu Lys Ser Tyr Glu
                245                 250
```

(2) INFORMATION FOR SEQ ID NO:58:

(i) SEQUENCE CHARACTERISTICS:
        (A) LENGTH: 201 amino acids
        (B) TYPE: amino acid
        (D) TOPOLOGY: unknown (ii) MOLECULE TYPE: protein (xi) SEQUENCE DESCRIPTION: SEQ ID NO:58:

```
Ser Phe Asn Leu Thr Thr Gly Asp Ser Gly Ala Phe Trp Thr Ile Ala
  1               5                  10                  15

Tyr Thr Ser Tyr Thr Asp Ala Leu Val Gln Val Glu Asn Thr Ala Ile
             20                  25                  30

Lys Lys Val Thr Tyr Cys Asn Ser His Ile Asn Asn Ile Lys Cys Ser
         35                  40                  45

Gln Leu Thr Ala Asn Leu Gln Asn Gly Phe Tyr Pro Val Ala Ser Ser
 50                  55                  60

Glu Val Gly Leu Val Asn Lys Ser Val Val Leu Leu Pro Ser Phe Tyr
 65                  70                  75                  80

Ser His Thr Ser Val Asn Ile Thr Ile Asp Leu Gly Met Lys Arg Ser
                 85                  90                  95

Gly Tyr Gly Gln Pro Ile Ala Ser Thr Leu Ser Asn Ile Thr Leu Pro
            100                 105                 110

Met Gln Asp Asn Asn Thr Asp Val Tyr Cys Ile Arg Ser Asn Gln Phe
            115                 120                 125

Ser Val Tyr Val His Ser Thr Cys Lys Ser Ser Leu Trp Asp Asp Val
130                 135                 140

Phe Asn Ser Asp Cys Thr Asp Val Leu Tyr Ala Thr Ala Val Ile Lys
145                 150                 155                 160

Thr Gly Thr Cys Pro Phe Ser Phe Asp Lys Leu Asn Asn Tyr Leu Thr
                165                 170                 175

Phe Asn Lys Phe Cys Leu Ser Leu Asn Pro Val Gly Ala Asn Cys Lys
            180                 185                 190

Phe Asp Val Ala Ala Arg Thr Arg Thr
            195                 200
```

(2) INFORMATION FOR SEQ ID NO:59:

(i) SEQUENCE CHARACTERISTICS:
        (A) LENGTH: 251 amino acids
        (B) TYPE: amino acid
        (D) TOPOLOGY: unknown (ii) MOLECULE TYPE: protein (xi) SEQUENCE DESCRIPTION: SEQ ID NO:59:

```
Glu Asn Met Glu Ile Asp Ser Met Leu Phe Val Ser Glu Asn Ala Leu
  1               5                  10                  15

Lys Leu Ala Ser Val Glu Ala Phe Asn Ser Thr Glu Thr Leu Asp Pro
             20                  25                  30

Ile Tyr Lys Glu Trp Pro Asn Ile Gly Gly Ser Trp Leu Gly Gly Leu
         35                  40                  45

Lys Asp Ile Leu Pro Ser His Asn Ser Lys Arg Lys Tyr Arg Ser Ala
 50                  55                  60

Ile Glu Asp Leu Leu Phe Asp Lys Val Val Thr Ser Gly Leu Gly Thr
 65                  70                  75                  80

Val Asp Glu Asp Tyr Lys Arg Cys Thr Gly Gly Tyr Asp Ile Ala Asp
                 85                  90                  95
```

-continued

```
Leu Val Cys Ala Gln Tyr Tyr Asn Gly Ile Met Val Leu Pro Gly Val
            100                 105                 110

Ala Asn Asp Asp Lys Met Ala Met Tyr Thr Ala Ser Leu Ala Gly Gly
            115                 120                 125

Ile Thr Leu Gly Ala Leu Gly Gly Ala Val Ser Ile Pro Phe Ala
    130                 135                 140

Ile Ala Val Gln Ala Arg Leu Asn Tyr Val Ala Leu Gln Thr Asp Val
145                 150                 155                 160

Leu Ser Lys Asn Gln Gln Ile Leu Ala Asn Ala Phe Asn Gln Ala Ile
            165                 170                 175

Gly Asn Ile Thr Gln Ala Phe Gly Lys Val Asn Asp Ala Ile His Gln
            180                 185                 190

Thr Ser Gln Gly Leu Ala Thr Val Ala Lys Ala Leu Ala Lys Val Gln
        195                 200                 205

Asp Val Val Asn Thr Gln Gly Gln Ala Leu Ser His Leu Thr Val Gln
    210                 215                 220

Leu Gln Asn Asn Phe Gln Ala Ile Ser Ser Ser Ile Ser Asp Ile Tyr
225                 230                 235                 240

Asn Arg Leu Asp Glu Leu Ser Ala Asp Ala Gln
                245                 250
```